United States Patent
Hsu et al.

(10) Patent No.: US 10,444,067 B2
(45) Date of Patent: Oct. 15, 2019

(54) OPTICAL SENSING APPARATUS AND MEASURING METHOD THEREOF

(71) Applicant: Industrial Technology Research Institute, Hsinchu (TW)

(72) Inventors: Chia-Hao Hsu, Tainan (TW); Chun-Te Chuang, Tainan (TW); Chih-Jen Chen, Tainan (TW); Yu-Tang Shen, Tainan (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 1110 days.

(21) Appl. No.: 14/583,770

(22) Filed: Dec. 29, 2014

(65) Prior Publication Data

US 2016/0120444 A1    May 5, 2016

(30) Foreign Application Priority Data

Oct. 31, 2014    (TW) .............................. 103137837 A

(51) Int. Cl.
*G01J 1/20*   (2006.01)
*G01J 1/32*   (2006.01)
(Continued)

(52) U.S. Cl.
CPC ............. *G01J 1/32* (2013.01); *A61B 5/14552* (2013.01); *A61B 5/681* (2013.01); *A61B 5/7221* (2013.01); *A61B 2562/0238* (2013.01)

(58) Field of Classification Search
CPC ........ A61B 5/11; A61B 5/0059; A61B 5/7275
See application file for complete search history.

(56) References Cited

U.S. PATENT DOCUMENTS 6,801,799 B2   10/2004   Mendelson
6,982,930 B1    1/2006   Hung
(Continued)

FOREIGN PATENT DOCUMENTS

CN    201870641    6/2011
CN    102389299    3/2012
(Continued)

OTHER PUBLICATIONS

"Office Action of Taiwan Counterpart Application", dated Feb. 18, 2016, p. 1-p. 15.

(Continued)

*Primary Examiner* — Joseph M Santos Rodriguez
(74) *Attorney, Agent, or Firm* — JCIPRNET

(57) ABSTRACT

An optical sensing apparatus including a light sensor, a plurality of light-emitting devices, and a controller is provided. The light sensor is disposed on a substrate. The light sensor senses a light reflection signal in a sensing area of the optical sensing apparatus. The light-emitting devices are disposed on the substrate and around the light sensor. The light-emitting devices provide an optical signal to be transmitted into the human tissue. Then, the optical signal is reflected by the human tissue to generate the light reflection signal. The controller determines whether the position of the human tissue has been changed in the sensing area. The controller drives at least one light-emitting device of the light-emitting devices and adjusts the light intensity thereof to provide the appropriate optical signal. Besides, a measuring method of the optical sensing apparatus is proposed.

27 Claims, 12 Drawing Sheets

(51) Int. Cl.
*A61B 5/00* (2006.01)
*A61B 5/1455* (2006.01)

(56) References Cited

U.S. PATENT DOCUMENTS

| | | | |
|---|---|---|---|
| 7,598,878 | B2 | 10/2009 | Goldreich |
| 7,729,748 | B2 | 6/2010 | Florian |
| 7,738,935 | B1 * | 6/2010 | Turcott ............... A61B 5/0261 600/336 |
| 8,055,321 | B2 | 11/2011 | Bernreuter |
| 8,086,301 | B2 | 12/2011 | Cho et al. |
| 8,100,834 | B2 | 1/2012 | Shuler |
| 8,172,761 | B1 | 5/2012 | Rulkov et al. |
| 8,401,608 | B2 | 3/2013 | Baker, Jr. et al. |
| 2002/0042558 | A1 | 4/2002 | Mendelson |
| 2003/0144584 | A1 | 7/2003 | Mendelson |
| 2005/0116820 | A1 | 6/2005 | Goldreich |
| 2006/0253010 | A1 | 11/2006 | Brady et al. |
| 2007/0106132 | A1 | 5/2007 | Elhag et al. |
| 2007/0197881 | A1 | 8/2007 | Wolf et al. |
| 2008/0051667 | A1 | 2/2008 | Goldreich |
| 2011/0082355 | A1 | 4/2011 | Eisen et al. |
| 2012/0150047 | A1 * | 6/2012 | Terumoto ........... A61B 5/02427 600/479 |
| 2013/0184544 | A1 | 7/2013 | Su et al. |
| 2014/0128691 | A1 | 5/2014 | Olivier |

FOREIGN PATENT DOCUMENTS

| | | |
|---|---|---|
| CN | 102551686 | 7/2012 |
| CN | 102688043 | 9/2012 |
| CN | 203303060 | 11/2013 |
| TW | M290417 | 5/2006 |
| TW | M333173 | 6/2008 |
| TW | I298630 | 7/2008 |
| TW | 200833297 | 8/2008 |
| TW | 201019900 | 6/2010 |
| TW | 201023823 | 7/2010 |
| TW | 201038253 | 11/2010 |
| TW | 201114404 | 5/2011 |
| TW | 201208648 | 3/2012 |
| TW | I379662 | 12/2012 |
| TW | 201306796 | 2/2013 |
| TW | 201309263 | 3/2013 |
| TW | 201310019 | 3/2013 |
| TW | 201315439 | 4/2013 |
| TW | 201338754 | 10/2013 |
| TW | 201347734 | 12/2013 |
| TW | I425934 | 2/2014 |
| TW | 201409014 | 3/2014 |
| TW | M478425 | 5/2014 |
| TW | 201424680 | 7/2014 |
| TW | M486395 | 9/2014 |
| TW | 201437978 | 10/2014 |
| TW | M487052 | 10/2014 |
| WO | 2013030744 | 3/2013 |

OTHER PUBLICATIONS

Li et al., "Onboard Tagging for Real-Time Quality Assessment of Photoplethysmograms Acquired by a Wireless Reflectance Pulse Oximeter," IEEE Transactions on Biomedical Circuits and Systems, Feb. 2012, pp. 54-63.

Li et al., "A Wireless Reflectance Pulse Oximeter With Digital Baseline Control for Unfiltered Photoplethysmograms," IEEE Transactions on Biomedical Circuits and Systems, Jun. 2012, pp. 269-278.

Cai et al., "Implementation of a Wireless Pulse Oximeter Based on Wrist Band Sensor," 2010 3rd International Conference on Biomedical Engineering and Informatics, Oct. 16-18, 2010, pp. 1897-1900.

Chen et al., "Non-invasive Blood Oxygen Saturation Monitoring for Neonates Using Reflectance Pulse Oximeter," Design, Automation & Test in Europe Conference & Exhibition (Date), Mar. 8-12, 2010. pp. 1530-1535.

Potuzakova et al., "Innovative Design for Monitoring of Neonates Using Reflectance Pulse Oximeter," 2011 Seventh International Conference on Intelligent Environments, Jul. 25-28, 2011, pp. 200-205.

Kejia Li et al., "Onboard Tagging for Real-Time Quality Assessment of Photoplethysmograms Acquired by a Wireless Reflectance Pulse Oximeter" IEEE Transactions on Biomedical Circuits and Systems, vol. 6, No. 1, Feb. 2012,pp. 54-63.

"Office Action of China Counterpart Application," dated Jan. 4, 2018, p. 1-p. 10.

Office Action of China Counterpart Application, dated Jul. 13, 2018, pp. 1-14.

* cited by examiner

OPTICAL SENSING APPARATUS AND MEASURING METHOD THEREOF

CROSS-REFERENCE TO RELATED APPLICATION

This application claims the priority benefit of Taiwan application serial no. 103137837, filed on Oct. 31, 2014. The entirety of the above-mentioned patent application is hereby incorporated by reference herein and made a part of specification.

TECHNICAL FIELD

The disclosure is relates to a sensing apparatus and a measuring method thereof and more particularly, to an optical sensing apparatus and a measuring method thereof.

BACKGROUND

Along with the development of humanities and technologies, the use of physiological healthcare apparatuses are no longer limited to the use in medical institutions, and physiological monitoring apparatuses are gradually used in families and sports facilities. Among them, wearable apparatuses have become important research subjects in recent years. A wearable wrist watch detecting a physiological signal by means of reflective optical detection is easily afflected by a wrist action and leads to an original measurement point shift, such that accuracy of signal analysis during exercise will be significantly affected. Therefore, current products available in the market are only adaptive for simple physiological signal detection functions, such as heart rate measurement.

Taking oxygen concentration detection for example, most commercially available non-invasive blood oxygen concentration meters are body-mounted finger-clip probe transmissive oximeters. The body-mounted finger-clip probe transmissive oximeters easily cause pressure on the finger if being used for a long time and result in poor circulation, which are quite uncomfortable for users. Moreover, most commercially available non-reflective blood oxygen concentration meters are worn on heads or attached to noses which have large-sized peripherals and bad portability, and are more adaptively for patients in bed. Comparatively, a wearable wrist physiological monitoring apparatus is a preferable solution for physiological monitoring in everyday life, which has advantages of convenient portability and is adaptive for being worn for a long time.

However, a wearable wrist watch is easily affected by a wrist action and leads to the original measurement point shift, such that the accuracy of signal analysis during exercise will be significantly affected.

SUMMARY

An optical sensing apparatus including at least one light sensor, a plurality of light-emitting devices and a controller is introduced herein. The light sensor is disposed on a substrate. The light sensor is configured to sense a light reflection signal in a sensing area of the optical sensing apparatus. The light-emitting devices are disposed on the substrate and around the at least one light sensor. The light-emitting devices are configured to provide an optical signal to be transmitted into a human tissue. The optical signal is reflected to generate the light reflection signal in the human tissue. The controller is electrically connected to the at least one light sensor and the light-emitting devices. The controller is configured to determine whether a position of the human tissue is changed in the sensing area. The controller drives at least one light-emitting device of the light-emitting devices according to the position of the human tissue in the sensing area, and the controller adjusts the light intensity of the at least one light-emitting device of the light-emitting devices to provide the optical signal.

A measuring method of an optical sensing apparatus is introduced herein. The method includes the following steps. A first combination of the light-emitting devices is driven, and light intensity of the first combination is adjusted to provide a first optical signal to be transmitted into a human tissue. The first light reflection signal generated by the first optical signal reflected the human tissue is sensed. Whether a position of the human tissue in a sensing area is changed is determined. If the position of the human tissue in the sensing area is changed, a second combination of the light-emitting devices is selected, and light intensity of the second combination is adjusted to provide a second optical signal to be transmitted into the human tissue. A second light reflection signal generated by the second optical signal reflected in the human tissue is sensed. Whether an amplitude of the second light reflection signal is within a predetermined range is determined. If the amplitude of the second light reflection signal is within the predetermined range, the second combination of the light-emitting devices is driven, the light intensity of the second combination is adjusted to provide the second optical signal. A physiological signal corresponding to the second light reflection signal having the amplitude within the predetermined range is calculated.

Several exemplary embodiments accompanied with figures are described in detail below to further describe the disclosure in details.

BRIEF DESCRIPTION OF THE DRAWINGS

The accompanying drawings are included to provide further understanding, and are incorporated in and constitute a part of this specification. The drawings illustrate exemplary embodiments and, together with the description, serve to explain the principles of the disclosure.

DETAILED DESCRIPTION OF DISCLOSED EMBODIMENTS

Figure 1:
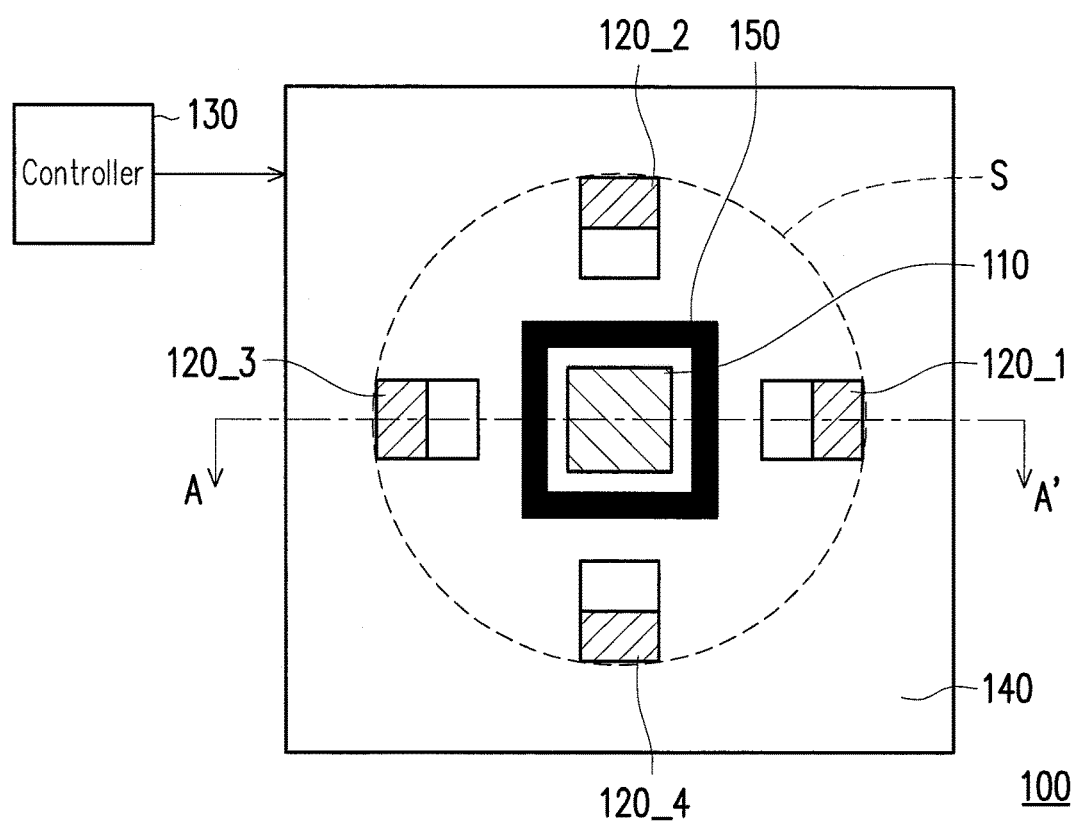
FIG. 1 is a schematic diagram illustrating an optical sensing apparatus according to an exemplary embodiment of the disclosure.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

The term "coupling/coupled" used in this specification (including claims) may refer to any direct or indirect connection means. For example, "a first device is coupled to a second device" is interpreted as "the first device is directly connected to the second device" or "the first device is indirectly connected to the second device through other devices or connection means." Moreover, wherever appropriate in the drawings and embodiments, elements/components/steps with the same reference numerals represent the same or similar parts. Elements/components/steps with the same reference numerals or names in different embodiments may be cross-referenced.

In the exemplary embodiments of the disclosure, an optical sensing apparatus may be applied to, for example, a wearable blood-oxygen monitoring watch, but the disclosure is not limited thereto. In a scenario of being applied in a wearable blood-oxygen monitoring watch, the optical sensing apparatus is configured to sense a light reflection signal generated by an optical signal reflected in a wrist artery. The light reflection signal serves as a physiological sensing signal at least containing physiological information, such as oxygen concentration. Thus, in the exemplary embodiments of the disclosure, a wrist artery is exemplarily illustrated as an example of a human tissue, but the disclosure is not limited thereto. Additionally, in a scenario where a human body posture changes, a weakeniness of signal intensity or a change of the signal waveform may propably occur to a light reflection signal of a blood vessel bio-signal due to the wrist artery shifting from a sensing point. Accordingly, the optical sensing apparatus does not continue to measure the blood vessel bio-signal. In this case, the change of the measurement position may lead to a poor signal-to-noise ratio (SNR) of the sensing signal or even a failure of sensing a physiological signal. Therefore, the search for the sensing point has to be conducted again, such that the signal may automatically return back to a measurable state to achieve continuous measurement. Accordingly, the optical sensing apparatus introduced by the exemplary embodiments of the disclosure is capable of performing a light source adjustment operation on a light emitting portion thereof and searching for measurement points of the blood vessel bio-signal in a sensing area by means of auto-tracking to automatically return back to a measurable state, so as to achieve continuous dynamic oxygen concentration detection. Therefore, the optical sensing apparatus introduced by the exemplary embodiments of the disclosure may be, for example, a dynamically reflective blood vessel bio-signal continuous monitoring device (dynamically reflective blood vessel bio-signal continuous monitoring device). Several exemplary embodiments are provided to describe the disclosure; however, the disclosure is not limited to the illustrated exemplary embodiments. Moreover, the illustrated exemplary embodiments are suitably combined.

Figure 2A:
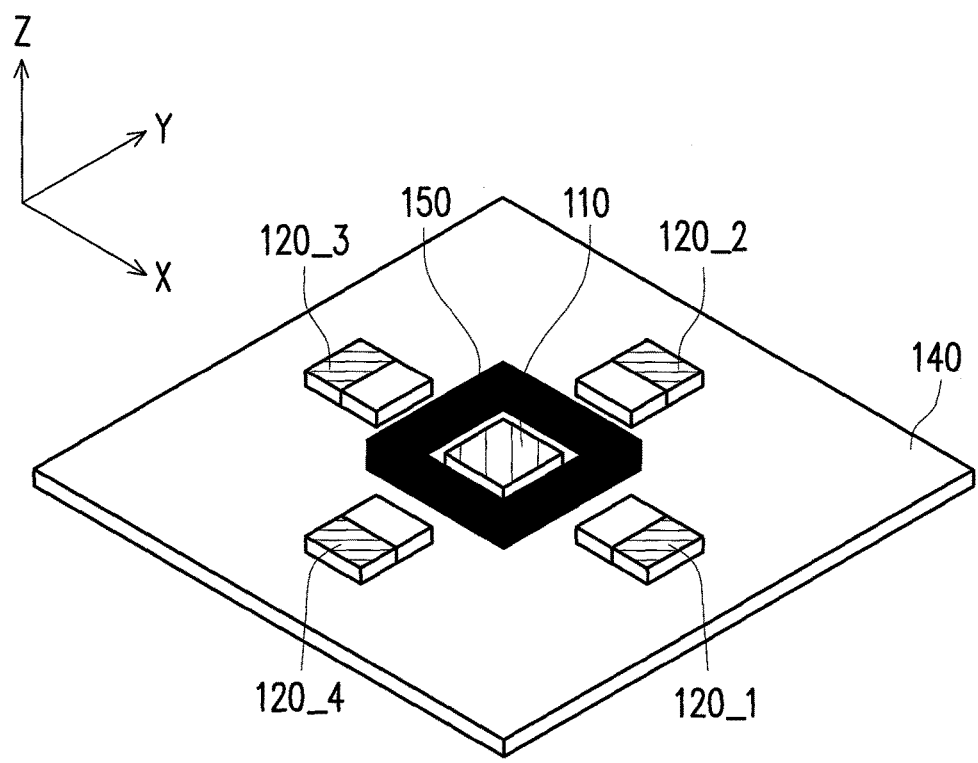
FIG. 2A and FIG. 2B are schematic diagrams respectively illustrating an optical module of the optical sensing apparatus depicted in FIG. 1 in different viewing angles.
Figure 2B:
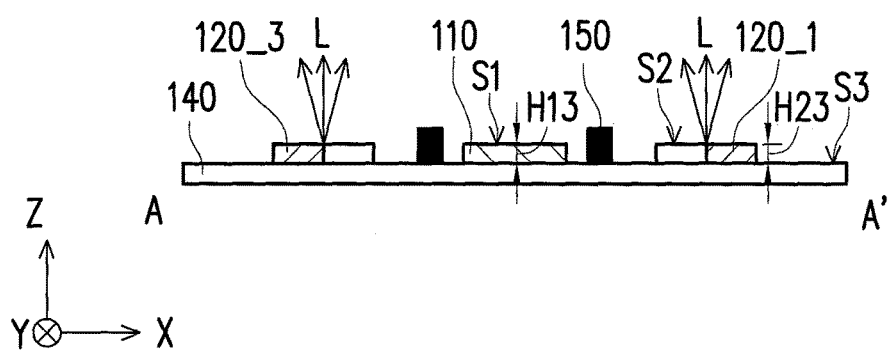

FIG. 1 is a schematic diagram illustrating an optical sensing apparatus according to an exemplary embodiment of the disclosure. FIG. 2A and FIG. 2B are schematic diagrams respectively illustrating an optical module depicted in FIG. 1 in different viewing angles. Herein, FIG. 2B is a schematic cross-sectional view illustrating the optical module depicted in FIG. 1 along line A-A'. With reference to FIG. 1 to FIG. 2B, an optical sensing apparatus 100 of the present exemplary embodiment includes at least one light sensor 110, a plurality of light-emitting devices 120_1 to 120_4 and a controller 130. In the present exemplary embodiment, an optical module includes the light sensor 110 and the light-emitting devices 120_1 to 120_4. The light sensor 110 is disposed on a substrate 140. The light-emitting devices 120_1 to 120_4 are disposed on the on the substrate 140 and around the light sensor 110. The controller 130 is electrically connected to the light sensor 110 and the light-emitting devices 120_1 to 120_4.

In the present exemplary embodiment, the light sensor 110 belonging to a light receiving portion is surrounded by the light-emitting devices 120_1 to 120_4 belonging to the light emitting portion. For example, in the present exemplary embodiment, the light sensor 110 is located between two light-emitting devices 120_1 and 120_3 among the light-emitting devices 120_1 to 120_4 in a first direction X and between the other two light-emitting device 120_2 and 120_4 among the light-emitting devices 120_1 to 120_4 in a second direction Y. In the present exemplary embodiment, the plurality of the light-emitting devices 120_1 to 120_4 and the manner of the light-emitting devices 120_1 to 120_4 surrounding the light sensor 110 are illustrated for example, but the disclosure is not limited thereto.

In the present exemplary embodiment, the controller 130 may be selectively embedded into the optical module, or separately disposed outside the optical module, which is not limited in the disclosure. In the present exemplary embodiment, the substrate 140 may be, for example, a flexible printed circuit board (FPCB) which serves as the substrate of the optical module, such that the optical sensing apparatus 100 may be attached with a human wrist surface. Additionally, a signal line may be embedded in the substrate 140, such that the substrate 140 may be electrically connected to the controller 130 through the signal line to transmit control signals to or receive the control signals from the controller 130.

In the present exemplary embodiment, the optical sensing apparatus 100 further includes a light isolation structure 150. The light isolation structure 150 is disposed on the substrate 140 and between the light sensor 110 and each of the light-emitting devices 120_1 to 120_4. The light isolation structure 150 is configured to isolate and shield an optical signal L provided by each of the light-emitting devices 120_1 to 120_4 from being transmitted into the light sensor 110. According to another aspect, the optical module of the present exemplary embodiment may further include the substrate 140 and the light isolation structure 150. In the present exemplary embodiment, the light isolation structure 150 may prevent the light sensor 110 from directly sensing a light source in a direct path of each of the light-emitting devices 120_1 to 120_4. Accordingly, the light sources received by the light sensor 110 are all reflected light sources from the human tissue. In addition, in the present exemplary embodiment, the light isolation structure 150 may also contribute to blocking an external ambient light source to prevent noise of the external ambient light source from interfering the sensing result of the light sensor 110. In the present exemplary embodiment, a material of the light isolation structure 150 may be, for example, a flexible rubber material. The light isolation structure 150 made of the flexible rubber material may be distributed, for example, around the light sensor 110 and expose a photosensitive area of the light sensor 110. Accordingly, the photosensitive area of the light sensor 110 may sense the light reflection signal inside the human tissue. Meanwhile, the light isolation structure 150 made of the flexible rubber material may be attached with a user's wrist surface to prevent the periphery of the light sensor 110 from harming the skin of the wrist surface, so as to improve wearing comfort.

In the present exemplary embodiment, the light-emitting devices 120_1 to 120_4 are configured to provide the optical signal L to be transmitted into the human tissue to detect a signal from the human tissue, e.g., a writs pulse signal. The optical signal L is reflected by the human tissue to generate a light reflection signal (e.g., a light reflection signal R illustrated in FIG. 5). The light sensor 110 is configured to sense a light reflection signal of the human tissue in a sensing area S. The controller 130 is configured to determine whether a position of the human tissue in the sensing area S is changed according to at least one of the light reflection signal and an action sensing signal. If a measurement condition deviates from an appropriate range, which leads to a failure of measuring the physiological signal, the controller 130 automatically adjusts the constituent devices contained in the combination of the light-emitting devices 120_1 to 120_4 and the light intensity thereof, so as to re-track the sensing position. Meanwhile, the controller 130 drives a combination of one or more light-emitting devices of the light-emitting devices 120_1 to 120_4 according to the position of the human tissue in the sensing area S. The controller 130 drives adjusts light intensity of the combination to provide the optical signal L. In the present exemplary embodiment, the combination of one or more light-emitting devices of the light-emitting devices may include, but the disclosure is not limited to any one, any two, any three or all of the light-emitting devices 120_1 to 120_4.

To be specific, in the present exemplary embodiment, the optical module includes the light sensor 110 and the light-emitting devices 120_1 to 120_4. The light-emitting devices 120_1 to 120_4 serve as a light emitting portion, for example, including a plurality of light-emitting devices with the same wavelength or different wavelengths. The light-emitting devices 120_1 to 120_4 are configured to emit the optical signal L with the same wavelength or different wavelengths to be transmitted into the human tissue. Meanwhile, the light-emitting devices 120_1 to 120_4 are independently controlled by the controller 130. Namely, one or more light-emitting device of the light-emitting devices 120_1 to 120_4 may be lighted up to provide the optical signal L, solely or simultaneously. In the present exemplary embodiment, the light sensor 110 serves as a light receiving portion and is configured to receive the light reflection signal generated by the optical signal L provided by the light-emitting devices 120_1 to 120_4 and reflected in the human tissue. In the present exemplary embodiment, the controller 130 serves as a signal controlling portion configured to drive the light-emitting devices 120_1 to 120_4 with the same wavelength or different wavelengths and capture a sensing signal, e.g., the light reflection signal, from the light sensor 110 of the light receiving portion. For example, in the present exemplary embodiment, after the signal is processed, the controller 130 performs a dynamical light adjustment operation on the light-emitting devices 120_1 to 120_4, so as to continuously measure the physiological signal including information, such as the oxygen concentration and a pulse rate of the wrist artery.

Figure 3A:
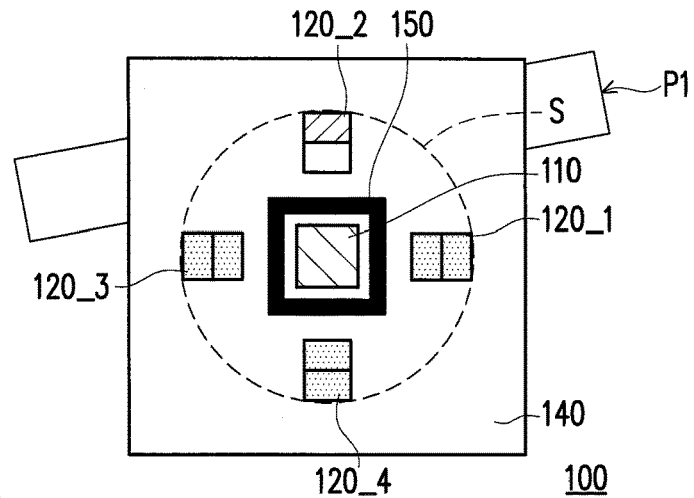
FIG. 3A to FIG. 3C are schematic diagrams illustrating the optical module of the optical sensing apparatus depicted in FIG. 1 measuring the human tissue.
Figure 3B:
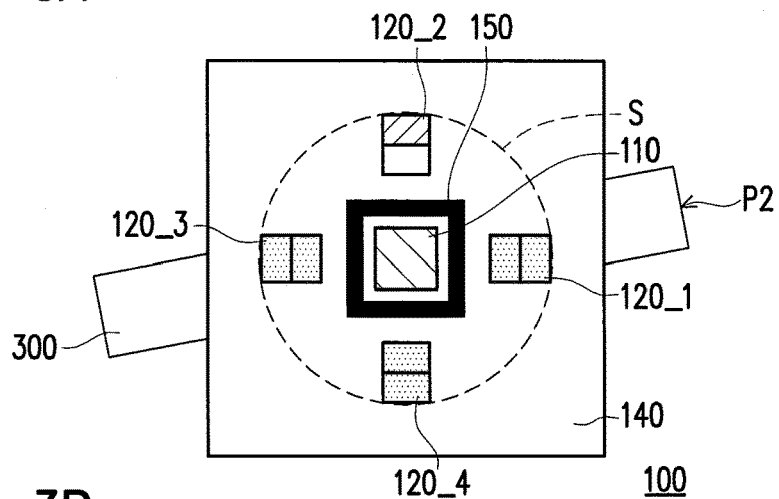
Figure 3C:
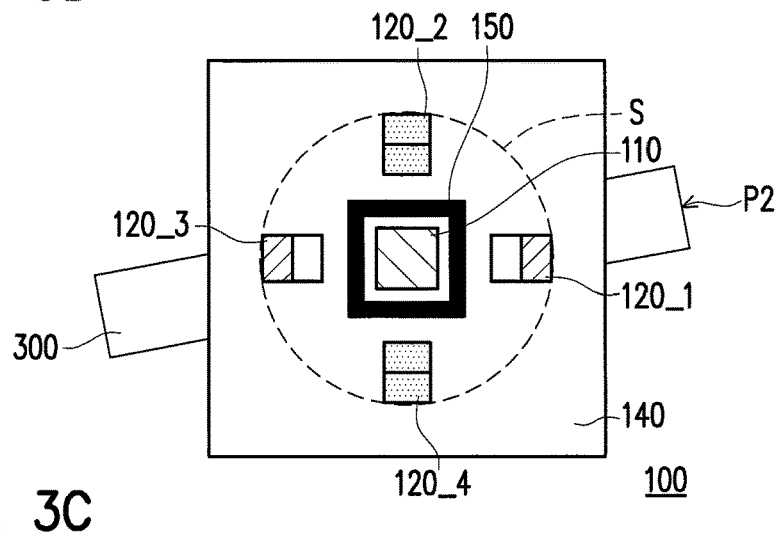

FIG. 3A to FIG. 3C are schematic diagrams illustrating the optical module of the optical sensing apparatus depicted in FIG. 1 measuring the human tissue. With reference to FIG. 1 through FIG. 3C, in FIG. 3A through FIG. 3C, the human tissue 300 (e.g., an artery) moves from a first position P1 to a second position P2 in the sensing area S. In the present exemplary embodiment, the controller 130 performs the light regulation on the light-emitting devices 120_1 to 120_4, so as to continuously and dynamically measure the oxygen concentration of the human tissue 300.

Specifically, referring to FIG. 3A, the human tissue 300 is located at the first position P1 in the sensing area S. The controller 130 selects the light-emitting device 120_2 to provide the optical signal L, such that the light-emitting device 120_2 is driven and lighted up. In this circumstance, if the human body posture is not changed, or the degree of the change of the human body posture is insufficient to affect the sensing result of the light sensor 110, the controller 130 processes the light reflection signal sensed by the light sensor 110 to obtain physiological information including a oxygen concentration and a pulse rate of the artery. In this case, the processed light reflection signal has an amplitude falling within a predetermined range. Such type of light reflection signal indicates that a blood vessel bio-signal included therein is recognizable, and characteristics of the blood vessel bio-signal are correct. Referring to FIG. 3A, while driving and lighting the light-emitting device 120_2 to provide the optical signal L, the controller 130 decreases light intensity of the rest of the light-emitting devices (i.e., the light-emitting devices 120_1, 120_3 and 120_4) among the light-emitting devices 120_1 to 120_4, which do not provide the optical signal L. When the light intensity of the light-emitting devices 120_1, 120_3 and 120_4 is decreased down to 0, it indicates that the controller 130 turns off the rest (i.e., the light-emitting devices 120_1 and 120_3 and 120_4) of the light-emitting devices 120_1 to 120_4, which do not provide the optical signal L.

Then, referring to FIG. 3B, the human tissue 300 moves from the first position P1 to the second position P2 in the sensing area S. In the circumstance, if the human body posture changes, or the degree of the change of the human body posture is sufficient to affect the sensing result of the light sensor 110, it indicates that the measurement of the optical sensing apparatus 100 is in an unstable transient state, and the amplitude of the processed light reflection signal is not within the predetermined range. Such type of light reflection signal indicates that the blood vessel bio-signal included therein is unrecognizable, and the characteristics of the blood vessel bio-signal are out of expectation. Thus, in the present exemplary embodiment, the controller 130 repeatedly performs the light adjustment operation on the light emitting portion. In the light adjustment operation, the controller 130 selects one or more light-emitting devices of the light-emitting devices 120_1 to 120_4 to serve as a combination and adjusts light intensity of the combination to provide the optical signal L. Next, the controller 130 drives and lights up the selected combination containing one or more light-emitting devices of the light-emitting devices. The combination containing one or more light-emitting devices of the light-emitting devices includes, for example, any one, any two, any three or all of the light-emitting devices 120_1 to 120_4. Thus, in the light adjustment operation, the light reflection signal sensed by the light sensor 110 is the optical signal L provided correspondingly by any one, any two, any three or all of the light-emitting devices 120_1 to 120_4. Thereafter, the controller 130 processes the light reflection signal sensed by the light sensor 110, such that the amplitude of the processed light reflection signal falls within the predetermined range. Such type of light reflection signal indicates that the blood vessel bio-signal included therein is recognizable, and the characteristics of the blood vessel bio-signal are correct. Further, the controller 130 selects the combination containing one or more light-emitting devices of the light-emitting devices providing the optical signal L corresponding to the recognizable light reflection signal. Next, the controller 130 adjusts the light intensity of the combination, such that the combination is driven and lighted up. In this case, the combination containing one or more light-emitting devices of the light-emitting devices providing the optical signal L corresponding to the recognizable light reflection signal may include, for example, the light-emitting devices 120_1 and 120_3.

Thus, referring to FIG. 3C, the human tissue 300 is located at the first position P1 in the sensing area S. The controller 130 selects the light-emitting devices 120_1 and 120_3 to provide the optical signal L and adjusts the light intensity of the light-emitting devices 120_1 and 120_3. Accordingly, the light-emitting devices 120_1 and 120_3 are driven and lighted up. The controller 130 processes the light reflection signal sensed by the light sensor 110 to obtain physiological information including the oxygen concentration of the wrist artery. In this case, the light emitting portion is processed by the light adjustment operation, and thus, the processed light reflection signal has an amplitude within the predetermined range. Such type of light reflection signal indicates that the blood vessel bio-signal included therein is recognizable, and the characteristics of the blood vessel bio-signal are correct. Referring to FIG. 3C, while driving and lighting the light-emitting devices 120_1 and 120_3 and adjusting the light intensity of the light-emitting devices 120_1 and 120_3 to provide the optical signal L, the controller 130 decreases light intensity of the rest of the light-emitting devices (i.e., the light-emitting devices 120_2 and 120_4) among the light-emitting devices 120_1 to 120_4, which do not provide the optical signal L. When the light intensity of the light-emitting devices 120_2 and 120_4 is decreased down to 0, it indicates that the controller 130 turns off the rest of the light-emitting devices (i.e., the light-emitting devices 120_2 and 120_4) among the light-emitting devices 120_1 to 120_4, which do not provide the optical signal L.

Accordingly, in the present exemplary embodiment, if the human tissue 300 is located at the first position P1, as shown in FIG. 3A, the controller 130 drives at least one first light-emitting device (e.g., the light-emitting device 120_2) of the light-emitting devices 120_1 to 120_4 and adjust light intensity of the first light-emitting device to provide the optical signal L. If the human tissue 300 is located at the second position P2, as ashown in FIG. 3C, the controller 130 drives at least one second light-emitting device (e.g., the light-emitting devices 120_1 and 120_3) of the light-emitting devices 120_1 to 120_4 and adjusts light intensity of the second light-emitting device to provide the optical signal L. In the present exemplary embodiment, the amount of the second light-emitting devices is 2, which is greater than the amount of the first light-emitting device, but the disclosure is not limited thereto. In the present exemplary embodiment, each light reflection signal generated by the the optical signal L reflected in the human tissue 300 located at the first position P1 and the second position P2 has an amplitude within the predetermined range, which is recognizable, and each light reflection signal has blood vessel bio-signal with correct characteristics.

In the present exemplary embodiment, a vertical distance H13 between a surface S1 of the light sensor 110 and a surface S3 of the substrate 140 is equal to a vertical distance H23 between a surface S2 of each of the light-emitting devices 120_1 to 120_4 between the surface S1 of the substrate 140. However, the disclosure is not limited thereto, and in another exemplary embodiment, the vertical distance H13 between the surface S1 of the light sensor 110 and the surface S3 of the substrate 140 may be greater than the vertical distance H23 between the surface S2 of each of the light-emitting devices 120_1 to 120_4 and the surface S1 of the substrate 140.

Figure 4:
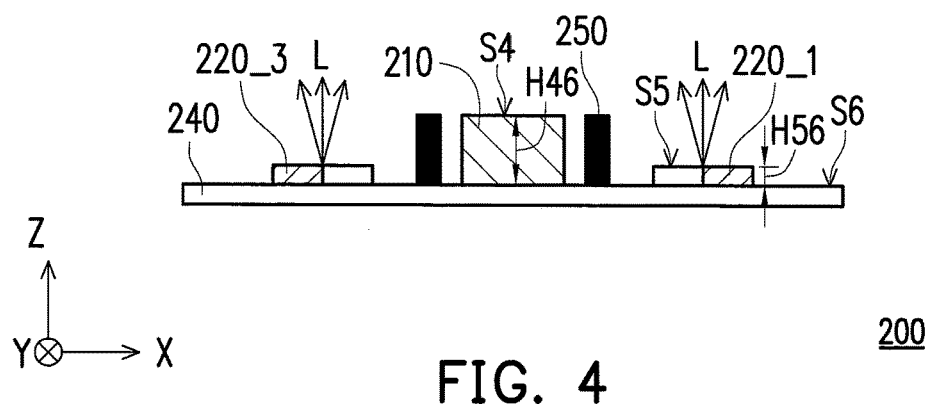
FIG. 4 is a schematic cross-sectional view illustrating an optical module of an optical sensing apparatus according to another exemplary embodiment of the disclosure.

FIG. 4 is a schematic cross-sectional view illustrating an optical module of an optical sensing apparatus according to another exemplary embodiment of the disclosure. With reference to FIG. 2B and FIG. 4, an optical module of an optical sensing apparatus 200 of the present exemplary embodiment is similar to the optical module of the optical sensing apparatus 100 depicted in FIG. 2B, but the difference therebetween lies in the following. The optical module of the optical sensing apparatus 200 of the present exemplary embodiment includes a light sensor 210, light-emitting devices 220_1 and 220_3 and another two light-emitting devices (not shown) arranged in the second direction Y. In the present exemplary embodiment, a vertical distance H46 between a surface S4 of the light sensor 210 and a surface S6 of a substrate 240 is greater than a vertical distance H56 between a surface S5 of each of the light-emitting devices 220_1 and 220_3 and a surface S6 of the substrate 240.

Figure 5:
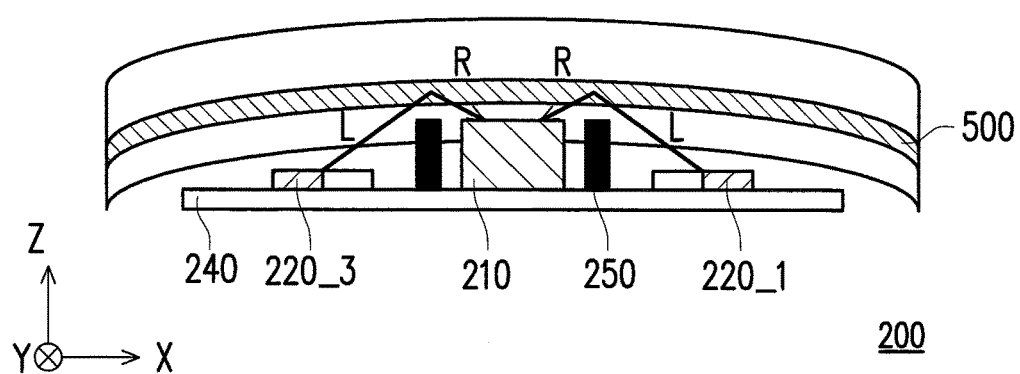
FIG. 5 is a schematic diagram illustrating the optical module of the optical sensing apparatus depicted in FIG. 4 measuring the human tissue.

FIG. 5 is a schematic diagram illustrating the optical module of the optical sensing apparatus depicted in FIG. 4 measuring the human tissue. With reference to FIG. 4 and FIG. 5, in the present exemplary embodiment, one way to increase the vertical distance H46 between the surface S4 of the light sensor 210 and the surface S6 of the substrate 240 is to pad up the bottom of the light sensor 210 with the use of the same material as the substrate 240, so as to increase the distance between the surface S4 of the light sensor 210 and the surface S6 of the substrate 240. However, the disclosure is not intent to limit the way to increase the vertical distance H46. In the present exemplary embodiment, the light sensor 210 is higher than each of the light-emitting devices 220_1 and 220_3. Thus, when the optical module of the optical sensing apparatus 200 measures a human tissue 500, e.g., a wrist artery, the light sensor 210 contacts with the human tissue 500 more closely to increase an SNR of the light sensor 210 receiving a light reflection signal R reflected in the human tissue 500, so as to enhance the light reflection signal R in the wrist.

Figure 6:
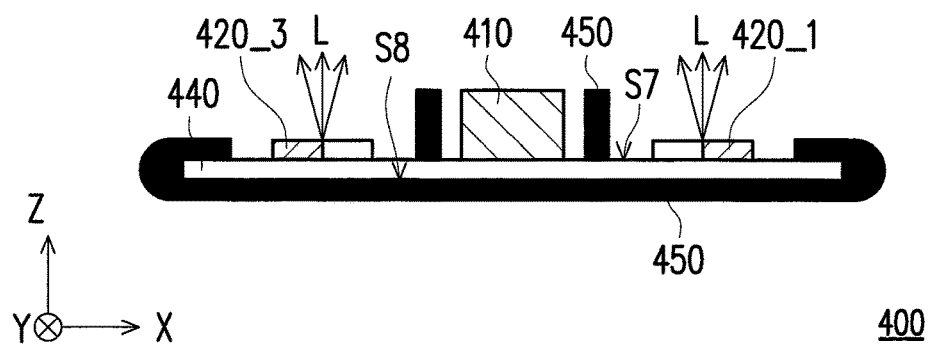
FIG. 6 is a schematic cross-sectional view illustrating an optical module of an optical sensing apparatus according to another exemplary embodiment of the disclosure.

FIG. 6 is a schematic cross-sectional view illustrating an optical module of an optical sensing apparatus according to another exemplary embodiment of the disclosure. With reference to FIG. 4 and FIG. 6, an optical module of an optical sensing apparatus 400 of the present exemplary embodiment is similar to the optical module of the optical sensing apparatus of the optical sensing apparatus 200 depicted in FIG. 4, but the difference therebetween lies in the following. The optical module of the optical sensing apparatus 400 of the present exemplary embodiment includes a light sensor 410, light-emitting devices 420_1 and 420_3 and another two light-emitting devices (not shown) arranged in the second direction Y. In the present exemplary embodiment, besides being disposed between the light sensor 410 on a substrate 440 and each of light-emitting devices 420_1 and 420_3, the light isolation structure 450 is also disposed on the other surface of the substrate 440 opposite to the surface that the light sensor 410 and each of the light-emitting devices 420_1 and 420_3 are disposed and cover. Specifically, in the present exemplary embodiment, the light sensor 410 and the light-emitting devices 420_1 and 420_3 are disposed, for example, on a first surface S7 of the substrate 440. The light isolation structure 450 is further on a second surface S8 of the substrate 440 and covers the second surface S8. In this case, the second surface S8 is opposite to the first surface S in the substrate 440.

Figure 7A:
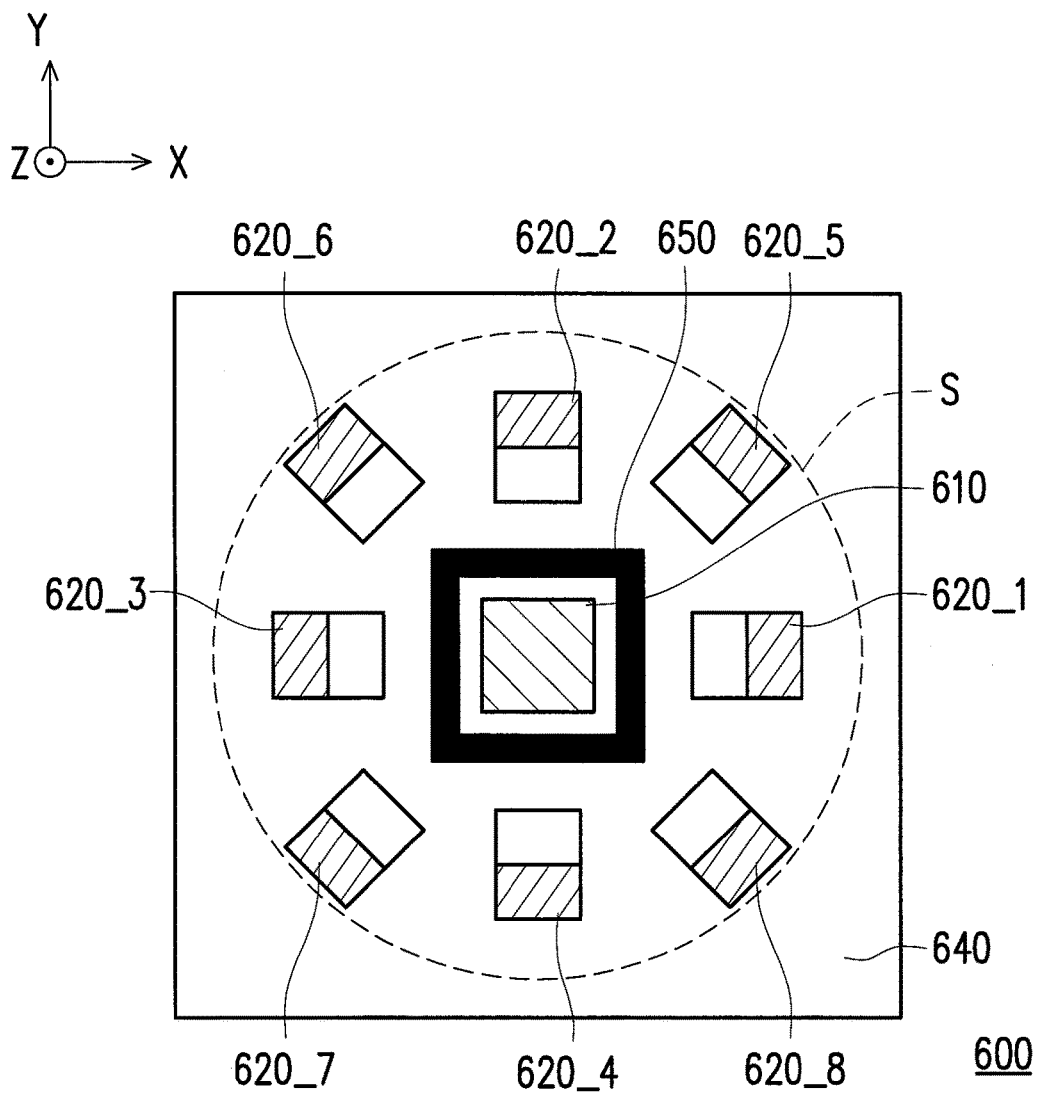
FIG. 7A is a schematic top view illustrating the optical module of the optical sensing apparatus according to another exemplary embodiment of the disclosure.

FIG. 7A is a schematic top view illustrating the optical module of the optical sensing apparatus according to another exemplary embodiment of the disclosure. With reference to FIG. 1 and FIG. 7A, an optical module of an optical sensing apparatus 600 of the present exemplary embodiment is similar to the optical module of the optical sensing apparatus 100 depicted in FIG. 1. The difference therebetween, for example, lies in the amount and the pattern of light-emitting devices disposed on a substrate 640. In the present exemplary embodiment, the optical module of the optical sensing apparatus 600 includes 8 light-emitting devices 620_1 to 620_8. Besides the light-emitting devices 620_1 to 620_4 which are disposed in the first direction X and the second direction Y, the light-emitting devices 620_5 and 620_8 further surround the light sensor 610 and are alternately interlaced with the light-emitting devices 620_1 to 620_4. A part or all of the the light-emitting devices 620_5 and 620_8 may cooperate with the light-emitting devices 620_1 to 620_4 to provide the optical signal L. In the present exemplary embodiment, the amount of the light-emitting devices 620_1 to 620_9 and the manner surrounding the light sensor 110 of the light-emitting devices 620_1 to 620_9 are illustrated for example, but the disclosure is not limited thereto.

Figure 7B:
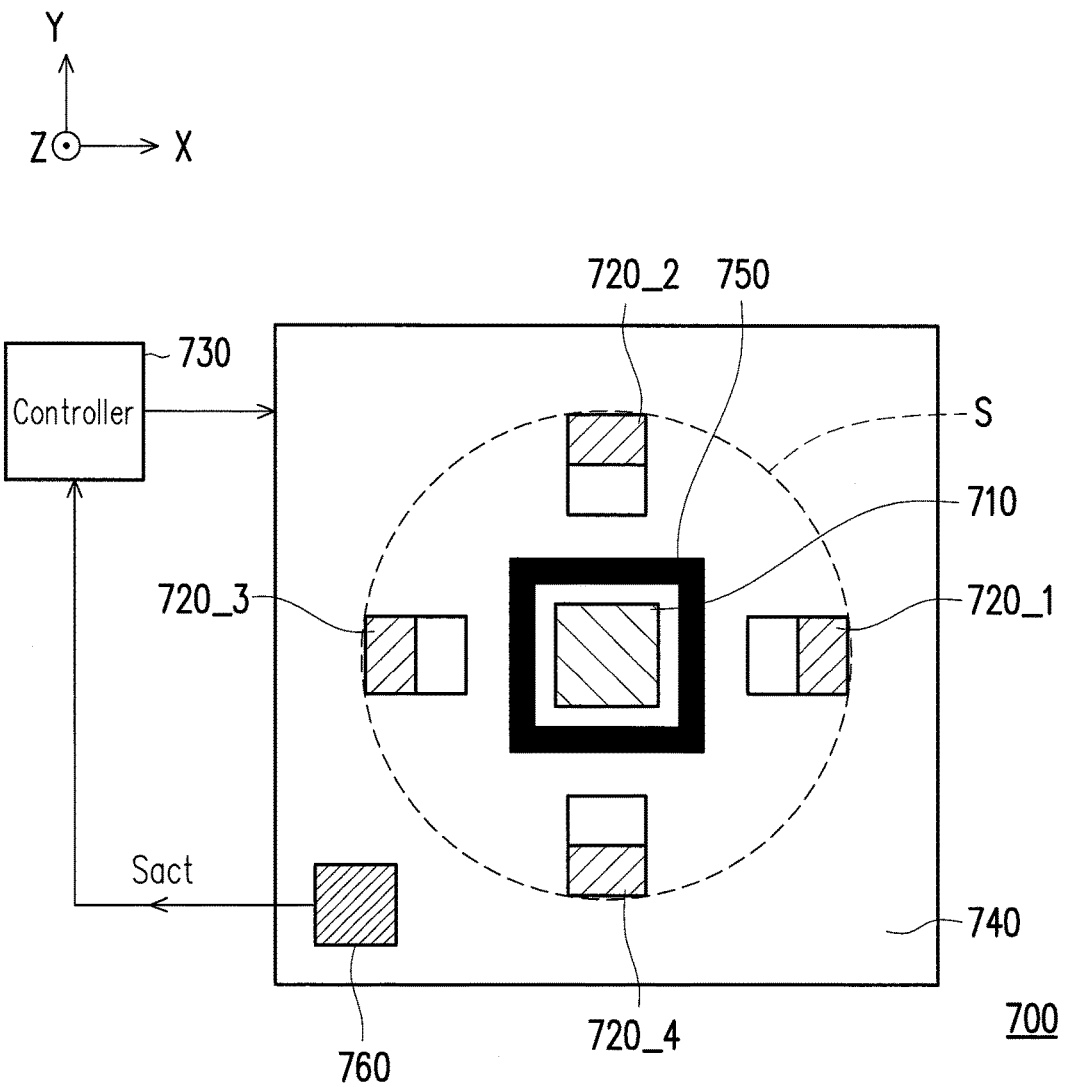
FIG. 7B is a schematic top view illustrating the optical module of the optical sensing apparatus according to another exemplary embodiment of the disclosure.

FIG. 7B is a schematic top view illustrating the optical module of the optical sensing apparatus according to another exemplary embodiment of the disclosure. With reference to FIG. 1 and FIG. 7B, an optical module of an optical sensing apparatus 700 of the present exemplary embodiment is similar to the optical module of the optical sensing apparatus 100 depicted in FIG. 1. The difference therebetween, for example, lies in that the optical sensing apparatus 700 further includes an action sensing device 760. In the present exemplary embodiment, the action sensing device 760 is disposed on a substrate 740 and configured to sense whether the position of the human tissue in the sensing area S is changed, so as to generate an action sensing signal Sact. In the present exemplary embodiment, the controller 130 determines whether the position of the human tissue in the sensing area S is changed, for example, according to at least one of the light reflection signal and the action sensing signal Sact. In the present exemplary embodiment, a position of the action sensing device 760 is illustrated as being disposed in the lower left corner of the substrate 740, but the disclosure is not limited thereto. In other exemplary embodiments, the action sensing device 760 may be disposed at any position on the substrate 740. Alternatively, the action sensing device 760 may be embedded in or mounted on any position of the substrate 740 in the optical sensing apparatus 700 that may sense whether the position of the human tissue in sensing area S is changed, but the disclosure is not limited thereto.

In the present exemplary embodiment, the action sensing device 760 may be, for example, an inertial device or a piezoelectric device, but the disclosure is not limited thereto. In an exemplary embodiment where the the action sensing device 760 is an inertial device, the action sensing device 760 senses a position offset of a measurement point that may be caused by instant acceleration. Namely, in this circumstance, the position of the human tissue in the sensing area S may be changed. In an exemplary embodiment where the the action sensing device 760 is a piezoelectric device, the action sensing device 760 may be, for example, a flexible piezoelectric tactile sensor configured to sense whether a position of a measurement point shifts. In an exemplary embodiment, the optical sensing apparatus 700 may also mechanically sense whether the position of the human tissue in the sensing area S changed. In this case, the action sensing device 760 may be, for example, a roller ball built in a mouse configured to determine a moving distance between positions of the roller ball moving on a surface where the roller ball contacts the skin, so as to determine whether the position of the measurement point shifts. In an exemplary embodiment, the optical sensing apparatus 700 may also sense whether the position of the human tissue in the sensing area S is changed by using sonic waves. In this case, the action sensing device 760 may be, for example, an ultrasonic displacement sensor.

In an exemplary embodiment, besides determining whether the position of the human tissue in the sensing area S is changed according to the light reflection signal, the optical sensing apparatus 700 may also determine whether the position of the human tissue in the sensing area S is changed in an optical manner. In this case, the optical sensing apparatus 700 may determine whether the position of the measurement point shifts by using an optical positioning technique.

Furthermore, in the optical sensing apparatus provided by each exemplary embodiment illustrated in FIG. 4, FIG. 6, FIG. 7A, FIG. 7B, the function, operation and implementation aspect thereof may refer to the teaching, suggestion and description of the exemplary embodiments illustrated in FIG. 1 through FIG. 3B and therefore, will not be repeatedly described herein.

Figure 8:
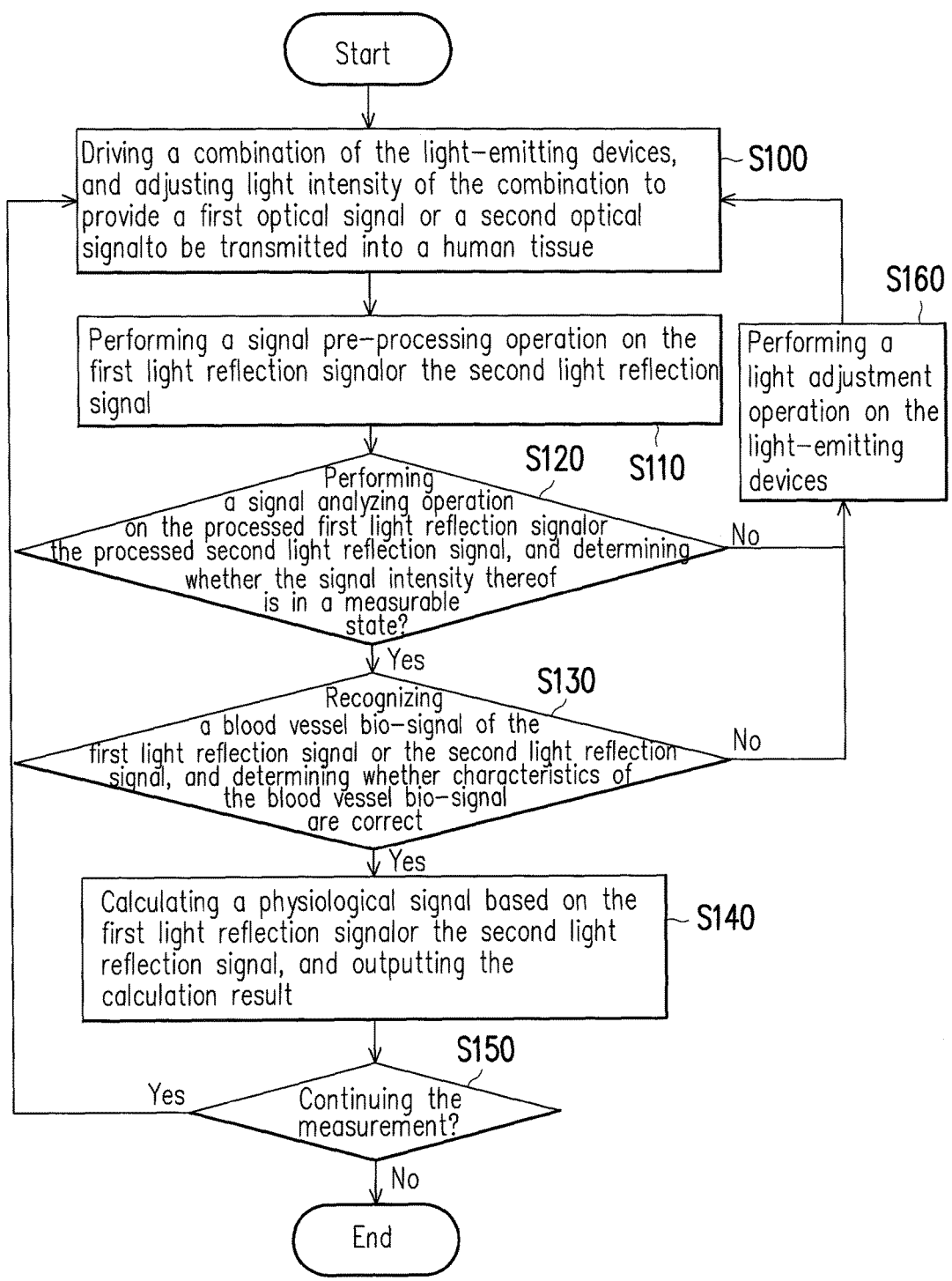
FIG. 8 is a flowchart of a measuring method of an optical sensing apparatus according to an exemplary embodiment of the disclosure.

FIG. 8 is a flowchart of a measuring method of an optical sensing apparatus according to an exemplary embodiment of the disclosure. With reference to FIG. 1 through FIG. 3C and FIG. 8, the measuring method of the present exemplary embodiment may be applied in the optical sensing apparatus 100 depicted in FIG. 1 and configured to measure the human tissue 300, for example. In the present exemplary embodiment, the optical sensing apparatus 100 may be, for example, a dynamically reflective blood vessel bio-signal continuous monitoring device, and the measuring method depicted in FIG. 8 may be, for example, a dynamically reflective blood vessel bio-signal continuous monitoring method.

In the present exemplary embodiment, an initial position of the human tissue 300 is at, for example, the first position P1 in the sensing area S, as shown in FIG. 3A. In step S100, the controller 130 drives a combination of the light-emitting devices 120_1 to 120_4 and adjusts light intensity of the combination to provide a first optical signal to be transmitted into the human tissue 300. For example, in step S100, the controller 130 selects the light-emitting device 120_2 and adjusts the light intensity of the light-emitting device 120_2 to provide the optical signal L, such that the light-emitting device 120_2 is driven and lighted up. Meanwhile, in step S100, the light sensor 110 senses the first light reflection signal generated by the the first optical signal reflected in the human tissue 300. In the present exemplary embodiment, the first light reflection signal is, for example, a physiological sensing signal corresponding to the first optical signal generated by the first optical signal reflected in the human tissue 300 at the initial position. The physiological sensing signal includes physiological information such as oxygen concentration and a pulse rate of the wrist artery at the first position P1.

Then, in step S110, the controller 130 performs a signal pre-processing operation on the first light reflection signal to obtain a processed first light reflection signal of the human tissue 300 in a stable state at the first position P1. In step S110, the signal pre-processing operation includes, but not limited to, a human body posture recognition step, a signal filtering step, a signal separating step. In the present exemplary embodiment, since the human tissue 300 is stable at the first position P1, the controller 130 determines that no change occurs to the human body posture in the step of recognizing whether the human body posture changes during the signal pre-processing operation. That is, in this circumstance, the human tissue 300 is, for example, stably located at the first position P1 without moving to another position (e.g., the second position P2). Alternatively, in an exemplary embodiment, in a situation where the degree of the change of the human body posture is insufficient to affect the sensing result of the light sensor 110, the human tissue 300 may also be considered as in a stable state. In step S110, if the human tissue 300 is determined as in the stable state, i.e., the position of the human tissue 300 in the sensing area S is not changed, the controller 130 performs step S120.

In step S110, if the human tissue 300 is determined as in an unstable state, e.g., in a transient state that the human tissue 300 moves from the first position P1 to the second position P2, or the human tissue 300 just arrives at the second position P2, but is still unstable, the controller 130 continuously performs the human body posture recognition step and then, performs step S120 until confirming that no change occurs to the position of the human tissue 300 in the sensing area.

Thereafter, in step S120, the controller 130 performs a signal analyzing operation on the processed first light reflection signal to determine whether signal intensity thereof is in a measurable state. For example, in the present exemplary embodiment, if an amplitude of the processed first light reflection signal is within a predetermined range, it indicates that the signal intensity of the first light reflection signal is measurable state. In step S120, if the signal intensity of the first light reflection signal is determined as in the measurable state, the controller 130 performs step S130.

In step S120, if the signal intensity of the first light reflection signal is determined as in an unmeasurable state, e.g., the amplitude of the processed first light reflection signal is out of the predetermined range, the controller 130 performs step S160 to perform the light adjustment operation on the light-emitting devices 120_1 to 120_4.

Afterwards, if the signal intensity of the first light reflection signal is in the measurable state, in step S130, the controller 130 recognizes the blood vessel bio-signal of the first light reflection signal, and determines whether characteristics of the blood vessel bio-signal are correct. In an exemplary embodiment of determining whether the characteristics of the blood vessel bio-signal are correct, the controller 130 may, for example, determine whether an absolute peak value, a relative peak value, an absolute trough value or a relative trough value of the amplitude of the first light reflection signal is within the predetermined range, or whether the four signal amplitude eigenvalues meet a predetermined relative relationship. In step S130, if the bloossel bio-signal of the first light reflection signal is determined as being correct, the controller 130 performs step S140. Otherwise, in step S130, if the bloossel bio-signal of the first light reflection signal is determined as being incorrect, the controller 130 performs step S160 to perform the light adjustment operation on the light-emitting devices 120_1 to 120_4.

Then, in step S140, the controller 130 calculates a physiological signal based on the first light reflection signal and then outputs the calculation result. Then, in step S150, the controller 130 determines whether to continue to measure the human tissue 300. If yes, the controller 130 returns to step S100 to repeatedly perform the process of the measuring method. If no, the controller 130 ends the process of the measuring method.

Figure 9:
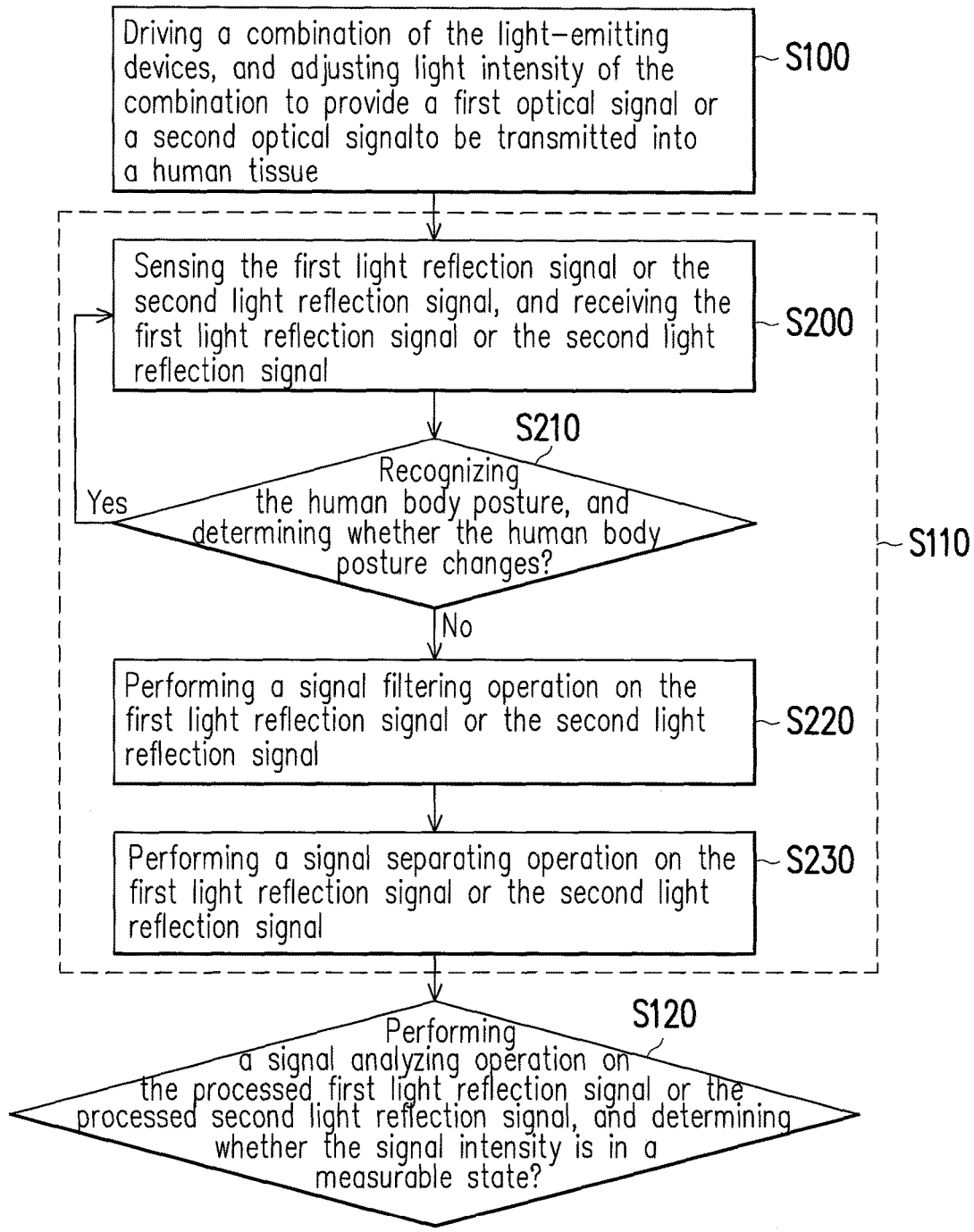
FIG. 9 is a flowchart of a signal pre-processing operation of the optical sensing apparatus according to an exemplary embodiment of the disclosure.

FIG. 9 is a flowchart of a signal pre-processing operation of the optical sensing apparatus according to an exemplary embodiment of the disclosure. With reference to FIG. 1 through FIG. 3C, FIG. 8 and FIG. 9, in step S110 depicted in FIG. 8, the controller 130 performs the signal pre-processing operation on the first light reflection signal to obtain the processed first light reflection signal of the human tissue 300 in the stable state at the first position P1. In the present exemplary embodiment, the signal pre-processing operation includes the following steps. In step S200, the controller 130 uses the light sensor 110 to sense the first light reflection signal and receives the first light reflection signal. In step S210, the controller 130 recognizes the human body posture and determines whether the human body posture changes, i.e., whether the position of the human tissue 300 in the sensing area S is changed. In step S210, if it is determined that the position of the human tissue 300 in the sensing area S is not changed, the controller 130 performs step S220. In step S220, the controller 130 performs a signal filtering operation on the first light reflection signal to filter out a noise component from the first light reflection signal and obtain signal components of the first light reflection signal. Then, in step S230, the controller 130 performs a signal separating operation on the first light reflection signal to separate an AC component from a DC component in the first light reflection signal to obtain the AC component of the first light reflection signal.

Figure 10:
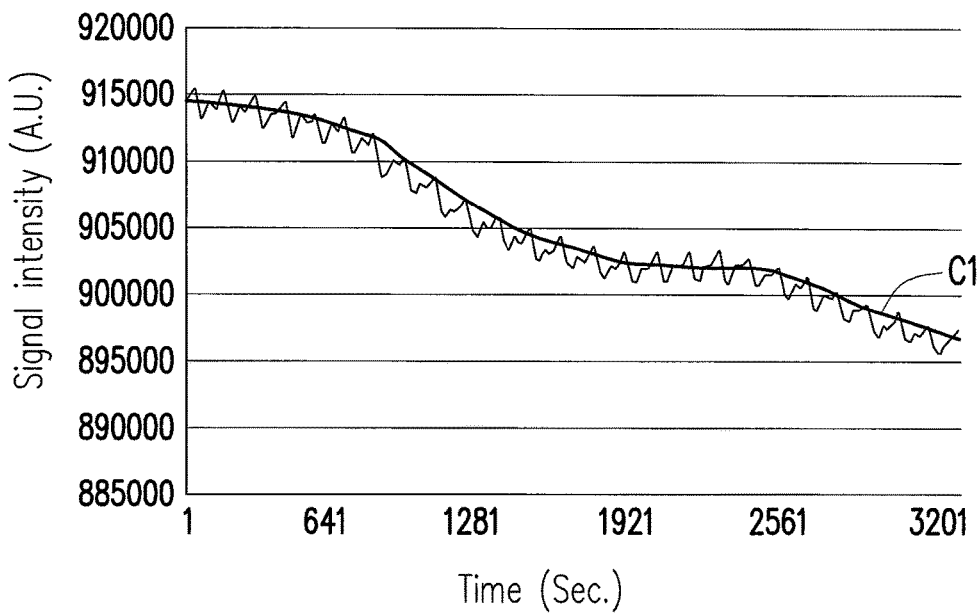
FIG. 10 and FIG. 11 are schematic waveform graphs of the first light reflection signal according to an exemplary embodiment of the disclosure.
Figure 11:
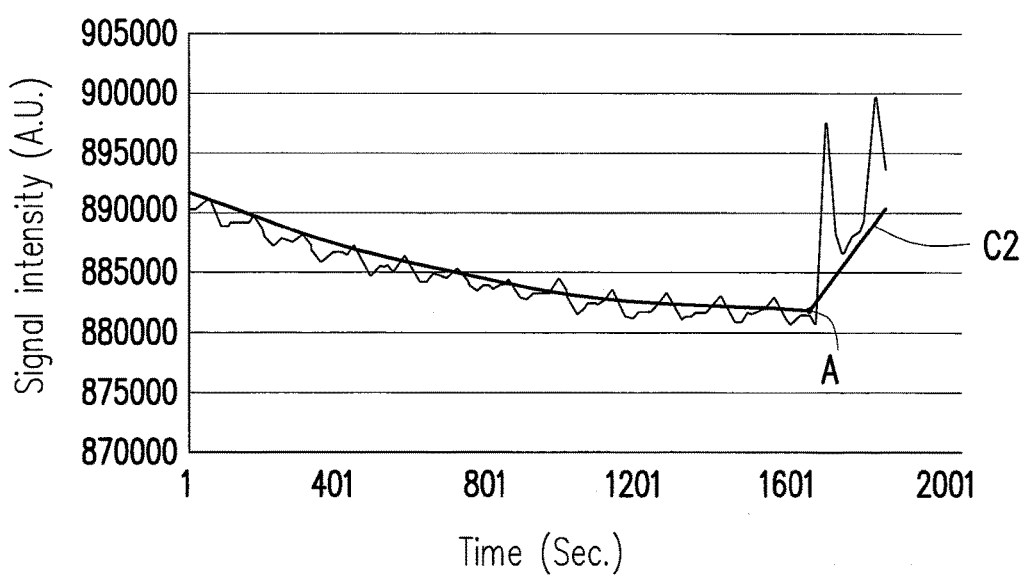

In the present exemplary embodiment, in step S210, in an exemplary embodiment of determining whether the position of the human tissue 300 in the sensing area S is changed, the determination is performed according to, for example, trend lines respectively corresponding to the first light reflection signal and the action sensing signal. FIG. 10 and FIG. 11 are schematic waveform graphs of the first light reflection signal according to an exemplary embodiment of the disclosure. With reference to FIG. 10 and FIG. 11, in the present exemplary embodiment, FIG. 10 and FIG. 11 respectively illustrate scenarios where the first light reflection signal corresponds to a trend line C1 and a trend line C2. In FIG. 10, the trend line C1 is a continuous curve. In this circumstance, the controller 130 determines that the position of the human tissue 300 in the sensing area S is not changed, or alternatively, even though the position of the human tissue 300 in the sensing area S is changed, the degree of change is insufficient to affect the sensing result of the light sensor 110. In other words, in the present exemplary embodiment, the trend line C1 depicted in FIG. 10 is a continuous and smooth curve, and during the determining period of the controller 130, a slope of the trend line C1 has no dramatical change. Thereby, the controller 130 determines that the position of the human tissue 300 in the sensing area S is not changed. In the present exemplary embodiment, even though the reference factor for the controller 130 to determine whether the position of the human tissue 300 is changed is the degree of the slope change of the trend line C1, the disclosure is not limited thereto. According to actual design requirements, any other curve parameter of trend line C1 may also be served for the determination of the controller 130, which is not limited in the disclosure.

Referring to FIG. 11, the trend line C2 includes a turning point A. In this circumstance, the controller 130 determines that the position of the human tissue 300 in the sensing area S is changed. For example, the human tissue 300 moves from the initial position (e.g., the first position P1 shown in FIG. 3A) to another position (e.g., the second position P2 shown in FIG. 3B or FIG. 3C) in the sensing area S. For example, when the human tissue 300 moves from the first position P1 to the second position P2 in the sensing area S, the turning point A is generated on the trend line C2. Namely, in the present exemplary embodiment, during the determining period of the controller 130, a dramatically change occurs to a slope of the trend line C2. Thus, the controller 130 determines that the position of the human tissue 300 in the sensing area S is changed. In the present exemplary embodiment, the generation of the turning point A is merely one of the dramatical changes that may possibly occur to the slope of the trend line C2, which are not limited in the disclosure. The dramatical changes occurring to the slope of the trend line C2 may be presented in other forms on the trend line C2. The aforementioned other forms may include, but not be limited thereto, other possible change forms, such as generating a singular point, a discontinuous point, a saddle point, or an inflection point on the trend line C2. In the present exemplary embodiment, even though the reference factor for the controller 130 to determine whether the position of the human tissue 300 is changed is the degree of the slope change of the trend line C2, but the disclosure is not limited thereto. According to actual design requirements, any other curve parameter of trend line C2 may also be served for the determination of the controller 130, which is not limited in the disclosure.

Additionally, in the disclosure, FIG. 10 and FIG. 11 only illustrate the schematic waveform graphs of the first light reflection signal, however, the determination whether the position of the human tissue 300 in the sensing area S is changed according to a trend line corresponding to the action sensing signal Sact may also be derived in the same way. For example, the trend line corresponding to the action sensing signal Sact may be similar those illustrated in one depicted in FIG. 10 and FIG. 11, and the operation may refer to the teaching, suggestion and description of the exemplary embodiments illustrated in FIG. 10 and FIG. 11 and therefore, will not be described herein.

Figure 12:
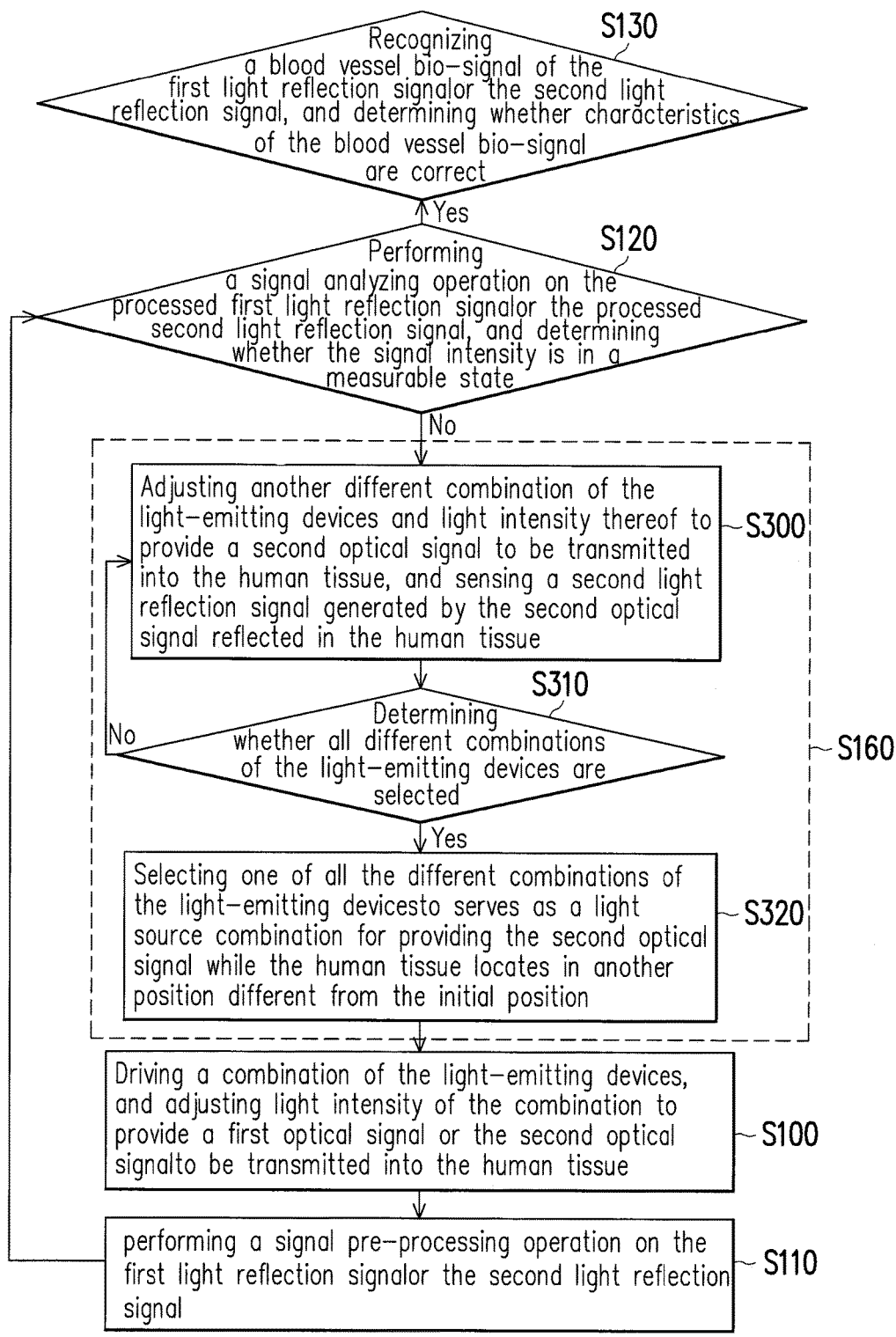
FIG. 12 is a flowchart of a light source adjustment operation of the optical sensing apparatus according to an exemplary embodiment of the disclosure.
Figure 13:
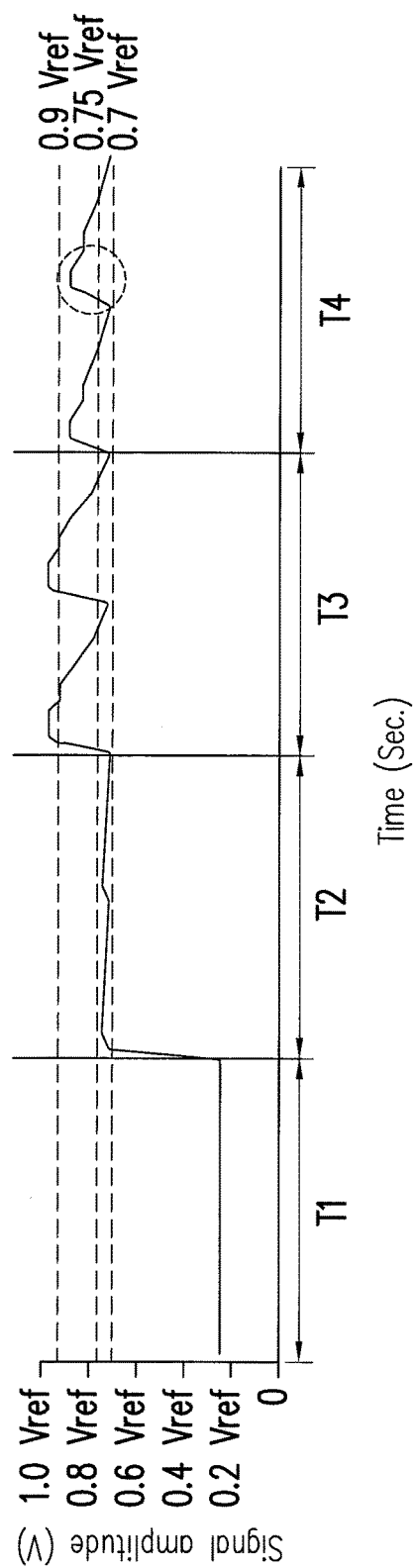
FIG. 13 is a schematic waveform graph of the light reflection signal during the light source adjustment operation according to an exemplary embodiment of the disclosure.

FIG. 12 is a flowchart of a light source adjustment operation of the optical sensing apparatus according to an exemplary embodiment of the disclosure. FIG. 13 is a schematic waveform graph of the light reflection signal during the light source adjustment operation according to an exemplary embodiment of the disclosure. With reference to FIG. 1 through FIG. 3C, FIG. 8, FIG. 12 and FIG. 13, in step S120 depicted in FIG. 8, one method performed by the controller 130 to determine whether the signal intensity of the first light reflection signal or the second light reflection signal is in the measurable state may, for example, determine whether the amplitude of the first light reflection signal or the second light reflection signal is within a predetermined voltage range from 0.7 Vref to 0.9 Vref, as shown in FIG. 13, where Vref refers to a reference voltage. In the present exemplary embodiment, taking the second light reflection signal as an example, the step of determining whether the amplitude of the second light reflection signal is within the predetermined voltage range from 0.7 Vref to 0.9 Vref by the controller 130 includes the following steps. First, the controller 130 determines whether a peak value of the amplitude of the second light reflection signal is less than an upper limit, i.e., 0.9 Vref, of the predetermined voltage range from 0.7 Vref to 0.9 Vref. Then, the controller 130 determines whether a trough value of the amplitude of the second light reflection signal is greater than a lower limit, i.e., 0.7 Vref, of the predetermined voltage range from 0.7 Vref to 0.9 Vref. In the present exemplary embodiment, the two steps are not sequentially related, and the predetermined voltage range 0.7 Vref to 0.9 Vref, the upper limit of 0.9 Vref and the lower limit of 0.7 Vref thereof are only provided for example, but the disclosure is not limited thereto.

In the present exemplary embodiment, when the human body posture changes, the signal intensity of the blood vessel bio-signal of the light reflection signal may be decreased, or the signal waveform thereof may be changed due to the wrist artery shifting from the sensing position. Accordingly, the optical sensing apparatus does not continue to measure the blood vessel bio-signal. For example, if the amplitude of the first light reflection signal is low (e.g., in a first stage T1 and a second stage T2 shown in FIG. 13), it may cause the controller 130 uneasily to recognize the characteristics of the blood vessel bio-signal, which indicates that the human body posture in this case may change, and reduction of the the signal intensity or change of signal waveform may occur to the first light reflection signal due to the wrist artery shifting from the sensing area S. If the amplitude of the first light reflection signal is within the predetermined voltage range from 0.7 Vref to 0.9 Vref (e.g., in a fourth stage T4 shown in the FIG. 13), it indicates that the signal intensity is in the measurable state, the controller 130 in this case performs step S130 depicted in FIG. 8. If the amplitude of the first light reflection signal of the second light reflection signal is out of the predetermined voltage range from 0.7 Vref to 0.9 Vref, the controller 130 performs step S300 and starts to perform the light adjustment operation on the light-emitting devices 120_1 to 120_4. Thus, in the disclosure, when the human body posture changes, the signal intensity of the blood vessel bio-signal of the light reflection signal may be decreased, or the signal waveform thereof may be changed due to the shift of the sensing position of the wrist artery. Accordingly, the optical sensing apparatus does not continue to measure the blood vessel bio-signal. In this case, the change of the measurement position may lead to a poor SNR of the sensing signal or even a failure of sensing the physiological signal, and therefore, the search for the sensing point has to be conducted again. Accordingly, the signal may automatically return back to a measurable state to achieve continuous measurement.

In step S300, the controller 130 adjusts another different combination of the light-emitting devices 120_1 to 120_4 and light intensity thereof to provide a second optical signal to be transmitted into the human tissue 300, and the controller 130 uses the light sensor 110 to sense a second light reflection signal generated by the second optical signal reflected in the human tissue 300. In the present exemplary embodiment, the second light reflection signal is a light reflection signal generated by the second optical signal reflected in the human tissue 300 at a position (e.g., the second position P2 shown in FIG. 3B or FIG. 3C) other than the initial position.

In the present exemplary embodiment, if a peak value of an amplitude of the second light reflection signal is greater than the upper limit 0.9 Vref (e.g., in a third stage T3 shown in FIG. 13) of the predetermined range, the controller 130 adjusts the constituent devices contained in the combination of the light-emitting devices 120_1 to 120_4 to decrease the peak value of the amplitude of the second light reflection signal. If a trough value of the amplitude of the second light reflection signal is lower than the lower limit 0.7 Vref (e.g., in the first stage T1 and the first stage T2 shown in FIG. 13) of the predetermined range, the controller 130 adjusts the constituent devices contained in the combination of the light-emitting devices 120_1 to 120_4 to increase the trough value of the amplitude of the second light reflection signal. In the present exemplary embodiment, in a scenario that the same combination of the light-emitting devices 120_1 to 120_4 is used, the method for the controller 130 to decrease the peak value of the amplitude of the second light reflection signal or to increase the trough value of the amplitude of the second light reflection signal may also be achieved by means of adjusting a driving current for the light-emitting devices 120_1 to 120_4 or adjusting a voltage gain of the second light reflection signal.

Then, in step S310, the controller 130 determines whether all different combinations of the light-emitting devices 120_1 to 120_4 are selected. In step S310, if it is determines that there are still different combinations of the light-emitting devices 120_1 to 120_4 unselected, the controller 130 continues to perform step S300. In step S310, if it is determined that all different combinations of the light-emitting devices 120_1 to 120_4 are selected, the controller 130 performs step S320.

In step S320, the controller 130 selects one of all the different combinations of the light-emitting devices 120_1 to 120_4 to serves as a light source combination for providing the second optical signal for the human tissue 300 at another position. In step S320, the second light reflection signal corresponding to the combination of the light-emitting devices 120_1 to 120_4 by the controller 130 is measured as being within the predetermined voltage range from 0.7 Vref to 0.9 Vref, in which the signal intensity is measurable. Thus, after the human tissue 300 moves from the initial position to another position, it is sure that the second light reflection signal is a reflection signal whose signal intensity is measurable after the controller 130 finishes the light adjustment operation. Then, the controller 130 returns to step S100 to drive the adjusted combination of the light-emitting devices and adjusts the light intensity of the combination to provide the second optical signal. Also, in the present exemplary embodiment, the second light reflection signal referred to in steps S110 and S120 is a light reflection signal generated by the the second optical signal reflected in the human tissue 300 after the human tissue 300 moves from the initial position to another position and stably stay there.

Figure 14:
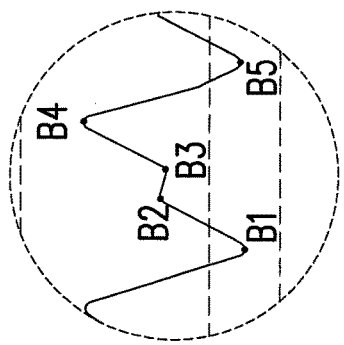
FIG. 14 is a schematic enlarged graph of part of the light reflection signal depicted in FIG. 13 in the fourth stage.

FIG. 14 is a schematic enlarged graph of part of the light reflection signal depicted in FIG. 13 in the fourth stage. With reference to FIG. 1, FIG. 8 and FIG. 13 through FIG. 14, in step S130 depicted in FIG. 8, the controller 130 recognizes the blood vessel bio-signal of the first light reflection signal or that of the second light reflection signal, and determines whether the characteristics of the blood vessel bio-signal are correct. Taking the second light reflection signal as an example, in an exemplary embodiment of determining whether the characteristics of the blood vessel bio-signal are correct, the controller 130 may, for example, determine whether an absolute peak value B4, a relative peak value B2, an absolute trough value B1 or B5 or a relative trough value B3 of the amplitude of the second light reflection signal is within the predetermined range or determine whether the four signal eigenvalues meet a predetermined relative relationship. For example, if the relative relationship of the four signal eigenvalues meets a predetermined relative relationship shown in FIG. 14, it indicates that the characteristics of the blood vessel bio-signal are correct, and the controller 130 continuously performs step S140 to calculate a physiological signal corresponding to the second light reflection signal and output the calculation result.

Figure 15:
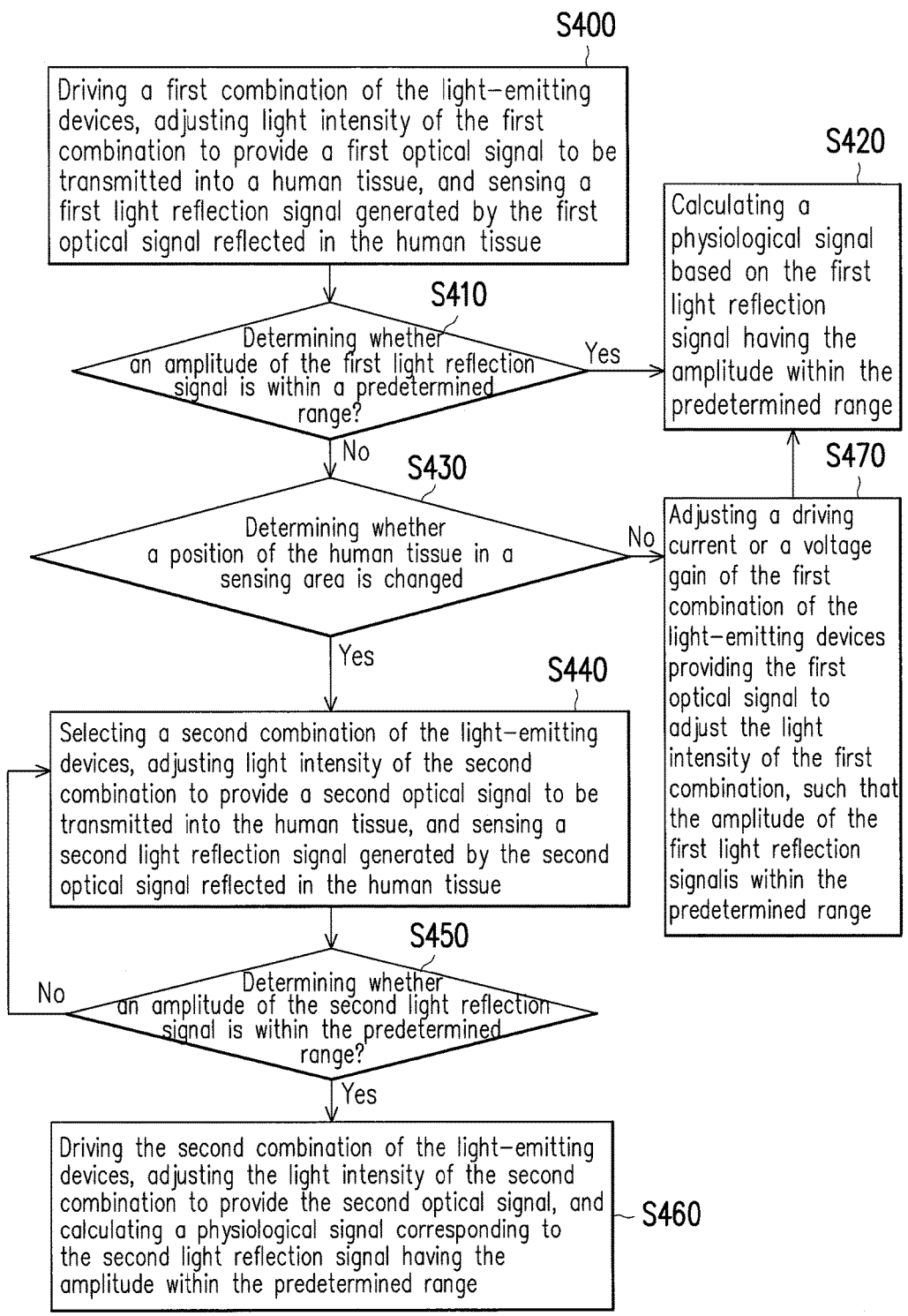
FIG. 15 is a flowchart of a measuring method of an optical sensing apparatus according to another exemplary embodiment of the disclosure.

FIG. 15 is a flowchart of a measuring method of an optical sensing apparatus according to another exemplary embodiment of the disclosure. With reference to FIG. 1 and FIG. 15, the measuring method of the present exemplary embodiment is applied, for example, in the optical sensing apparatus 100 depicted in FIG. 1 and configured to measure the human tissue 300. In the present exemplary embodiment, the optical sensing apparatus 100 may be, for example, a dynamically reflective blood vessel bio-signal continuous monitoring device, and the measuring method depicted in FIG. 15 may be, for example, a dynamically reflective blood vessel bio-signal continuous monitoring method.

In step S400, the controller 130 drives a first combination of the light-emitting devices 120_1 to 120_4 and adjusts light intensity thereof to provide a first optical signal to be transmitted into the human tissue 300, and the controller 130 senses a first light reflection signal generated by the first optical signal reflected in the human tissue 300. In step S410, the controller 130 determines whether an amplitude of the first light reflection signal is within a predetermined range. If yes, in step S420, the controller 130 calculates a physiological signal corresponding to the first light reflection signal having the amplitude within the predetermined range. If the amplitude of the first light reflection signal is out of the predetermined range, the controller 130 performs step S430. In step S430, the controller 130 determines whether a position of the human tissue 300 in the sensing area S is changed according to the first light reflection signal, an action sensing signal or both. In the present exemplary embodiment, the first light reflection signal is a light reflection signal generated by the first optical signal reflected in the human tissue 300 at an initial position (e.g., the first position P1 shown in FIG. 3A) in the sensing area S.

If the position of the human tissue 300 in the sensing area S is changed, the controller 130 performs step S440. In step S440, the controller 130 selects a second combination of the light-emitting devices 120_1 to 120_4 and adjusts light intensity of the second combination to provide a second optical signal to be transmitted into the human tissue 300, and the controller 130 uses the light sensor 110 to sense a second light reflection signal generated by the second optical signal reflected in the human tissue 300. Then, in step S450, the controller 130 determines whether an amplitude of the second light reflection signal is within the predetermined range. If the amplitude of the second light reflection signal is within the predetermined range, the controller 130 performs step S460. In step S460, the controller 130 drives the adjusted combination of the light-emitting devices 120_1 to 120_4 and adjusts the light intensity of the combination to provide the second optical signal, and the controller 130 calculates a physiological signal corresponding to the second light reflection signal having the amplitude within the predetermined range. In the present exemplary embodiment, the second light reflection signal is a light reflection signal generated by the first optical signal reflected in the human tissue 300 at another position (e.g., the second position P2 shown in FIG. 3B or FIG. 3C) in the sensing area S.

If the amplitude of the second light reflection signal is not within the predetermined range, the controller 130 returns to step S440 to repeatedly perform step S450, until the adjusted combination of light-emitting devices includes all combinations of one or more of the light-emitting devices 120_1 to 120_4. Thus, in step S460, the controller 130 selects to drive one of the combinations of the light-emitting devices 120_1 to 120_4. The amplitude of the second light reflection signal corresponding to the second optical signal provided by the adjusted combination of the light-emitting devices 120_1 to 120_4 is within in the predetermined range. In another exemplary embodiment, the controller 130 may also repeatedly perform step S450, until the amplitude of the second light reflection signal corresponding to the the adjusted combination of the light-emitting devices 120_1 to 120_4 falls within the predetermined range. In this circumstance, it is unnecessary for the controller 130 to try all the combinations of the light-emitting devices.

In step S430, if determining that the position of the human tissue 300 in the sensing area S is not changed, the controller 130 performs step S470. In step S470, the controller 130 adjusts a driving current or a voltage gain of the combination of the light-emitting devices providing the first optical signal to adjust the light intensity of the combination, and thereby, the amplitude of the first light reflection signal falls within the predetermined range. Then, the controller 130 performs step S420 to calculate a physiological signal corresponding to the first light reflection signal having the amplitude within the predetermined range.

In the present exemplary embodiment, the first optical signal and the second optical signal are, for example, optical signals provided by different combinations of the light-emitting devices at different times. For example, the first light reflection signal and the second light reflection signal may be light reflection signals respectively correspondingly generated by the first optical signal and the second optical signal reflected in the human tissue, which are generated in the manners shown in FIG. 5. Furthermore, in the exemplary embodiments of the disclosure, the first combination and the second combination may be formed by selecting one to a plurality of the light-emitting devices, and both may have the same or different constituent components.

Additionally, the measuring method of the present exemplary embodiment of the optical sensing apparatus may refer to the teaching, suggestion and description of the exemplary embodiments illustrated in FIG. 1 through FIG. 14 and therefore, will not be described herein.

To summarize, in the optical sensing apparatus and the measuring method thereof introduced by the disclosure, the combination of the light-emitting devices and the light intensity thereof for providing the optical signal are adjusted according to whether the position of the human tissue in the sensing area is changed. The optical sensing apparatus and the measuring method thereof introduced by the disclosure utilize the light adjustment operation to facilitate the light sensor to sense that the light reflection signals of the human tissue at different positions are in the measurable state.

It will be apparent to those skilled in the art that various modifications and variations can be made to the structure of the disclosed embodiments without departing from the scope or spirit of the disclosure. In view of the foregoing, it is intended that the disclosure cover modifications and variations of this disclosure provided they fall within the scope of the following claims and their equivalents.

What is claimed is:

1. An optical sensing apparatus, comprising:
   at least one light sensor, disposed on a substrate and configured to sense a light reflection signal in a sensing area of the optical sensing apparatus;
   a plurality of light-emitting sources, disposed on the substrate and around the at least one light sensor and configured to provide an optical signal to be transmitted into a human tissue, wherein the optical signal is reflected to generate the light reflection signal in the human tissue;
   a controller, electrically connected to the at least one light sensor and the light-emitting sources and configured to determine whether a position of the human tissue is changed in the sensing area according to the light reflection signal, wherein the controller drives at least one light-emitting source of the light-emitting sources and adjusts light intensity of the at least one of the light-emitting sources to provide the optical signal according to the position of the human tissue in the sensing area; and
   at least one light isolation wall, disposed between and spaced apart from the at least one light sensor and each of the light-emitting sources on the substrate, wherein the at least one light isolation wall is configured to isolate any optical signal, generated by any of the plurality of the light-emitting sources and not reflected from the human tissue, from being transmitted into the at least one light sensor.

2. The optical sensing apparatus according to claim 1, wherein the at least one light sensor is located between two light-emitting sources of the light-emitting sources in a first direction and between another two light-emitting sources of the light-emitting sources in a second direction.

3. The optical sensing apparatus according to claim 1, wherein a vertical distance between a surface of the at least one light sensor and a surface of the substrate is equal to a vertical distance between a surface of each of the light-emitting sources and the surface of the substrate.

4. The optical sensing apparatus according to claim 1, wherein a vertical distance between a surface of the light sensor and a surface of the substrate is greater than a vertical distance between a surface of each of the light-emitting sources and the surface of the substrate.

5. The optical sensing apparatus according to claim 1, wherein the at least one light sensor and the light-emitting sources are disposed on a first surface of the substrate, the at least one light isolation wall is further disposed on a second surface of the substrate opposite to the first surface, and the at least one light isolation wall covers the second surface.

6. The optical sensing apparatus according to claim 1, wherein the controller determines whether the position of the human tissue in the sensing area is changed according to at least one of the light reflection signal and an action sensing signal.

7. The optical sensing apparatus according to claim 6, further comprising:
an action sensing device, disposed on the substrate and configured to sense whether the position of the human tissue in the sensing area is changed, so as to generate the action sensing signal.

8. The optical sensing apparatus according to claim 6, wherein the light reflection signal and the action sensing signal respectively correspond to trend lines, if each of the trend lines is a continuous curve, the controller determines that the position of the human tissue in the sensing area is not changed according to at least one of the light reflection signal and the action sensing signal.

9. The optical sensing apparatus according to claim 6, wherein the light reflection signal and the action sensing signal respectively correspond to trend lines, if each of the trend lines comprises a turning point, the controller determines that the position of the human tissue in the sensing area is changed according to at least one of the light reflection signal and the action sensing signal.

10. The optical sensing apparatus according to claim 9, wherein the position comprises a first position and a second position, when the human tissue moves from the first position to the second position in the sensing area, the turning point is correspondingly generated in each of the trend lines.

11. The optical sensing apparatus according to claim 10, wherein if the human tissue is located at the first position, the controller drives at least one first light-emitting source among the light-emitting sources and adjusts light intensity of the at least one first light-emitting sources to provide the optical signal, and if the human tissue is located at the second position, the controller drives at least one second light-emitting source among the light-emitting sources and adjusts light intensity of the at least one second light-emitting source to provide the optical signal.

12. The optical sensing apparatus according to claim 11, wherein an amount of the at least one second light-emitting source is greater than an amount of the at least one first light-emitting source.

13. The optical sensing apparatus according to claim 1, wherein when the controller drives the at least one light-emitting source and adjusts the light intensity of the at least one light-emitting source to provide the optical signal, the controller decreases light intensity of the rest of the light-emitting sources of the light-emitting sources which do not provide the optical signal.

14. The optical sensing apparatus according to claim 1, wherein an amplitude of the light reflection signal generated by the optical signal reflected in the human tissue is within a predetermined range.

15. The optical sensing apparatus according to claim 1, wherein
the controller drives a combination of the light-emitting sources and adjusts light intensity of the combination to provide the optical signal to be transmitted into the human tissue, and uses the at least one light sensor to sense the light reflection signal generated by the optical signal reflected in the human tissue; the controller determines whether the position of the human tissue in the sensing area is changed; if the position of the human tissue in the sensing area is changed, the controller adjusts the light-emitting sources contained in the combination of the light-emitting sources and the light intensity of the combination to provide the optical signal to be transmitted into the human tissue, and uses the at least one light sensor to sense the light reflection signal generated by the optical signal reflected in the human tissue; the controller determines whether an amplitude of the light reflection signal is within a predetermined range; and if the amplitude of the light reflection signal is within the predetermined range, the controller drives the adjusted light-emitting sources contained in the combination of the light-emitting sources, adjusts the light intensity of the combination to provide the optical signal and calculates a physiological signal corresponding to the light reflection signal having the amplitude within the predetermined range.

16. A measuring method of an optical sensing apparatus, wherein the optical sensing apparatus comprises a plurality of light-emitting sources, the measuring method comprising:
driving a first combination of the light-emitting sources, adjusting light intensity of the first combination to provide a first optical signal to be transmitted into a human tissue, and sensing a first light reflection signal generated by the first optical signal reflected in the human tissue;
determining whether a position of the human tissue in a sensing area is changed according to the first light reflection signal;
if the position of the human tissue in the sensing area is changed, selecting a second combination of the light-emitting sources, adjusting light intensity of the second combination to provide a second optical signal to be transmitted into the human tissue, and sensing a second light reflection signal generated by the second optical signal reflected in the human tissue;
determining whether an amplitude of the second light reflection signal is within a predetermined range;
if the amplitude of the second light reflection signal is within the predetermined range, driving the second combination of the light-emitting sources, adjusting the light intensity of the second combination to provide the second optical signal, and calculating a physiological signal corresponding to the second light reflection signal having the amplitude within the predetermined range; and
gradually decreasing light intensity of the rest of the light-emitting sources which do not provide the first optical signal nor the second optical signal.

17. The measuring method according to claim 16, wherein the step of determining the amplitude of the second light reflection signal is within the predetermined range comprises:
determining whether a peak value of the second light reflection signal is lower than an upper limit of the predetermined range; and
determining whether a trough value of the second light reflection signal is higher than a lower limit of the predetermined range.

18. The measuring method according to claim 16, wherein the step of selecting the second combination from the light-emitting sources and adjusting the light intensity of the second combination comprises:
if the peak value of the second light reflection signal is higher than the upper limit of the predetermined range, adjusting the light-emitting sources contained in the second combination of the light-emitting sources and adjusting the light intensity of the second combination to decrease the peak value of the second light reflection signal; and if the trough value of the second light reflection signal is lower than the lower limit of the predetermined range, adjusting the light-emitting sources contained in the second combination of the light-emitting sources and adjusting the light intensity of the second combination to increase the trough value of the second light reflection signal.

19. The measuring method according to claim 16, further comprising:
if the amplitude of the second light reflection signal is out of the predetermined range, repeatedly performing the step of selecting the second combination from the light-emitting sources and adjusting the light intensity of the second combination, until the second combination of the light-emitting sources comprises all combinations of one or more light-emitting sources of the light-emitting sources.

20. The measuring method according to claim 16, further comprising:
if the amplitude of the second light reflection signal is out of the predetermined range, repeatedly performing the step of selecting the second combination from the light-emitting sources and adjusting the light intensity of the second combination, until the amplitude of the second light reflection signal corresponding to the second combination of the light-emitting sources falls within the predetermined range.

21. The measuring method according to claim 16, wherein the step of determining whether the position of the human tissue in the sensing area is changed comprises:
determining whether the position of the human tissue in the sensing area is changed according to at least one of the first light reflection signal and an action sensing signal.

22. The measuring method according to claim 21, wherein the first light reflection signal and the action sensing signal respectively correspond to trend lines, and the step of determining the position of the human tissue in the sensing area is changed comprises:
if each of the trend lines is a continuous curve, determining that the position of the human tissue in the sensing area is not changed.

23. The measuring method according to claim 21, wherein the first light reflection signal and the action sensing signal respectively correspond to trend lines, and the step of determining the position of the human tissue in the sensing area is changed comprises:
if each of the trend lines comprises a turning point, determining that the position of the human tissue in the sensing area is change.

24. The measuring method according to claim 23, wherein the position of the human tissue comprises a first position and a second position, when the human tissue moves from the first position to the second position in the sensing area, the turning point is generated each of the trend lines.

25. The measuring method according to claim 16, further comprising:
determining whether an amplitude of the first light reflection signal is within the predetermined range; and
if the amplitude of the first light reflection signal is within the predetermined range, calculating a physiological signal corresponding to the first light reflection signal having the amplitude within the predetermined range.

26. The measuring method according to claim 25, further comprising:
if the amplitude of the first light reflection signal is out of the predetermined range, performing the step of determining whether the position of the human tissue in the sensing area is changed.

27. The measuring method according to claim 16, further comprising:
if the position of the human tissue in the sensing area is not changed, adjusting a driving current or a voltage gain of the first combination of the light-emitting sources providing the first optical signal to adjust the light intensity of the first combination, such that the amplitude of the first light reflection signal is within the predetermined range.

\* \* \* \* \*